US011291712B2

(12) United States Patent
Rather et al.

(10) Patent No.: US 11,291,712 B2
(45) Date of Patent: Apr. 5, 2022

(54) BACTERIAL PROTEIN COMPOSITIONS AND USES THEREOF

(71) Applicants: The United States Government as Represented by the Department of Veterans Affairs, Washington, DC (US); EMORY UNIVERSITY, Atlanta, GA (US)

(72) Inventors: Philip Rather, Dunwoody, GA (US); David Weiss, Decatur, GA (US); Chui-Yoke Chin, Atlanta, GA (US); Kyle Tipton, Decatur, GA (US)

(73) Assignee: THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 16/647,692

(22) PCT Filed: Sep. 19, 2018

(86) PCT No.: PCT/US2018/051768
§ 371 (c)(1),
(2) Date: Mar. 16, 2020

(87) PCT Pub. No.: WO2019/060428
PCT Pub. Date: Mar. 28, 2019

(65) Prior Publication Data
US 2020/0276293 A1    Sep. 3, 2020

Related U.S. Application Data

(60) Provisional application No. 62/561,199, filed on Sep. 20, 2017.

(51) Int. Cl.
| | |
|---|---|
| *C12Q 1/68* | (2018.01) |
| *A61K 39/02* | (2006.01) |
| *A61K 47/55* | (2017.01) |
| *A61P 31/04* | (2006.01) |
| *A61K 35/74* | (2015.01) |
| *C07K 14/21* | (2006.01) |
| *A61K 38/00* | (2006.01) |
| *A61K 39/00* | (2006.01) |

(52) U.S. Cl.
CPC ............. *A61K 39/02* (2013.01); *A61K 35/74* (2013.01); *A61K 47/552* (2017.08); *A61P 31/04* (2018.01); *C07K 14/212* (2013.01); *A61K 38/00* (2013.01); *A61K 2039/522* (2013.01); *A61K 2039/542* (2013.01); *A61K 2039/545* (2013.01)

(58) Field of Classification Search
None
See application file for complete search history.

(56) References Cited

U.S. PATENT DOCUMENTS

| | | |
|---|---|---|
| 6,562,958 B1 | 5/2003 | Breton et al. |
| 2016/0324951 A1 | 11/2016 | Skaar et al. |
| 2017/0065700 A1 | 3/2017 | Vaxdyn et al. |

FOREIGN PATENT DOCUMENTS

| | | |
|---|---|---|
| CA | 3076594 | 9/2018 |
| EP | 18858834.7 | 9/2018 |
| WO | 2017004545 | 1/2017 |
| WO | PCT/US18/51768 | 9/2018 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Ainsworth et al., "Vaccination with a live attenuated Acinetobacter baumannii deficient in thioredoxin provides protection against systemic Acinetobacter infection" Vaccine, Jun. 8, 2017 (Aug. 6, 2017), vol. 35, No. 26, pp. 3387-3394.
Chin et al., "A high-frequency phenotypic switch links bacterial virulence and environmental survival in Acinetobacter baumannii" Nature Microbiology, vol. 3, May 2018 pp. 563-569 Epub Apr. 23, 2018.
Rosenfeld et al., "Expression of the Resistance-Nodulation-Cell Division Pump AdeIJK in Acinetobacter baumannii is Regulated by AdeN, a TetR-Type Regulator." Antimicrobial Agents and Chemotherapy, Feb. 27, 201 (Feb. 27, 2012), vol. 56, No. 5, p. 2504-2510.
Saranathan et al., "Disruption of tetR type regulator adeN by mobile genetic element confers elevated virulence in Acinetobacter baumannii" Virulence, Apr. 24, 2017 (Apr. 24, 20107), vol. 8, No. 7, pp. 1316-1334).
S.E. Anderson, "Regulation of a virulence switch in Acinetobacter baumannii" Talk and Abstract: 12th International Symposium on the Biology of Acinetobacter. Frankfort, Germany. 2019. Invited keynote speaker.
WP_001133118: TetR/AcR family transcriptional regulator [Acinetobacter baumannii]. Retrieved from the internet: <> on Nov. 15, 2018 (Nov. 15, 2018).

(Continued)

*Primary Examiner* — Jennifer E Graser
(74) *Attorney, Agent, or Firm* — Ballard Spahr LLP

(57) ABSTRACT

Disclosed herein is an attenuated *Acinetobacter baumannii* comprising an expression vector comprising a nucleic acid encoding the ABUW_1645 protein or a variant thereof. Disclosed herein are methods of treating or preventing colonization, infection, or disease by an *Acinetobacter baumannii* microbe, the method comprising administering a clinically effective dose of the attenuated *Acinetobacter baumannii* to a subject in need thereof, wherein the attenuated *Acinetobacter baumannii* comprises an expression vector expressing the ABUW_1645 protein or variants thereof.

7 Claims, 15 Drawing Sheets

Specification includes a Sequence Listing.

(56) References Cited

OTHER PUBLICATIONS

International Search Report and Written Opinion dated Dec. 4, 2018 by the International Searching Authority for International Patent Application No. PCT/US2018/051768, which was filed on Sep. 19, 2018 (Inventor—Philip Rather et al.; (Applicant—United States Government as Represented by the Department of Veterans Affairs, Inc.; (13 pages).
U.S. Appl. No. 62/561,199, filed Sep. 20, 2017, Philip Rather, et al.

* cited by examiner

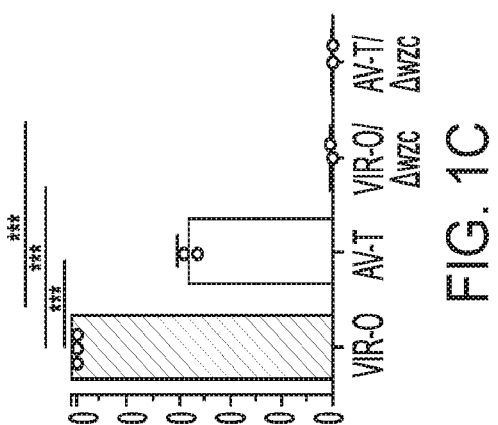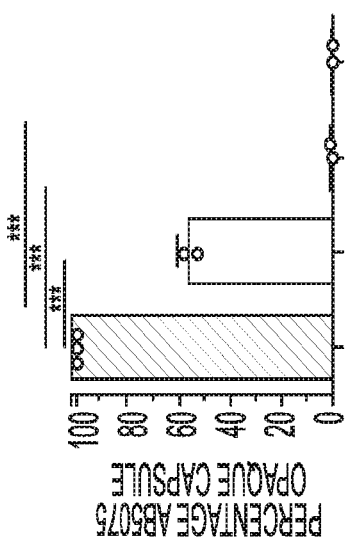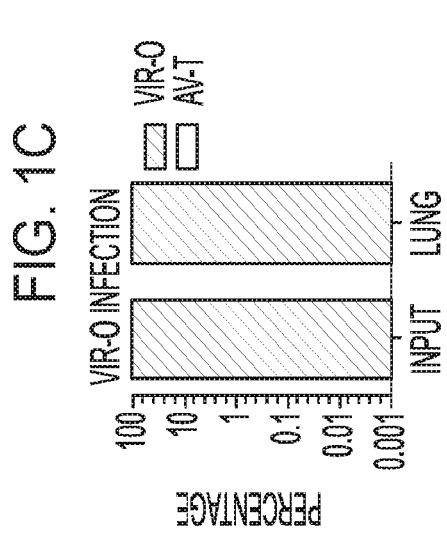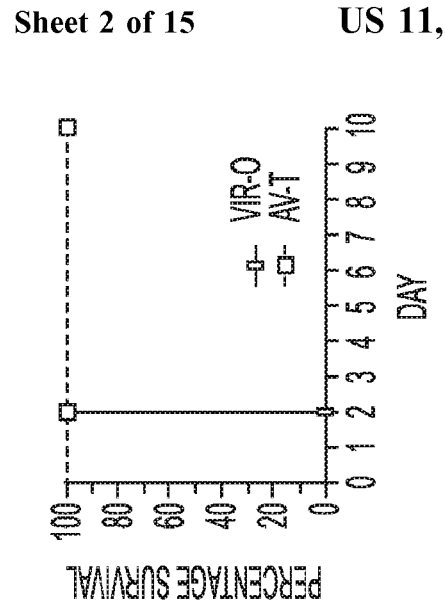

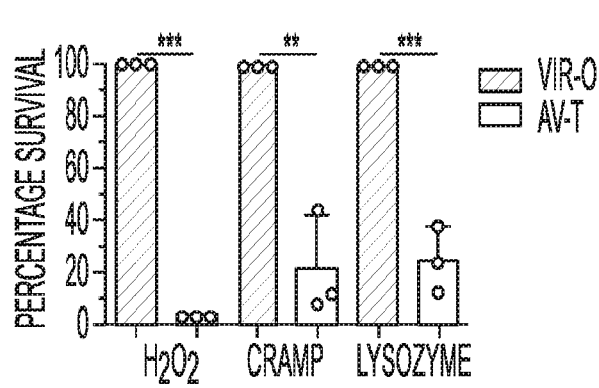
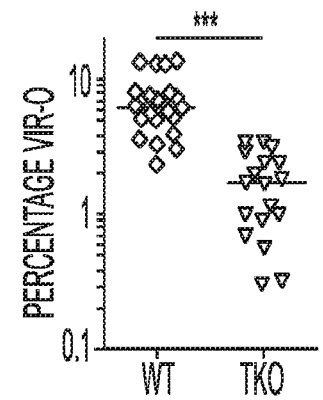
FIG. 2A   FIG. 2B
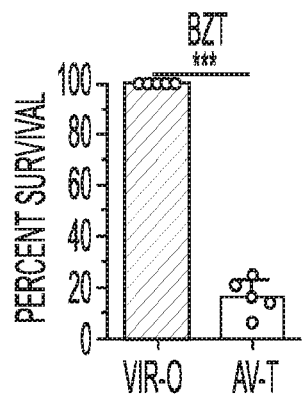
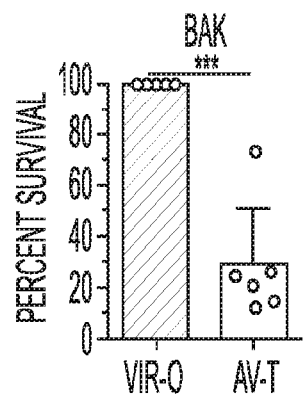
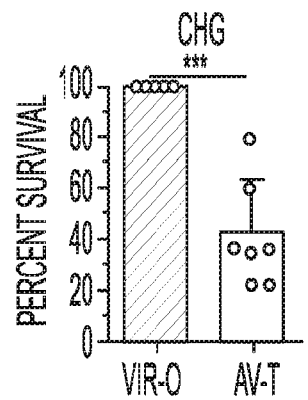
FIG. 2C   FIG. 2D   FIG. 2E
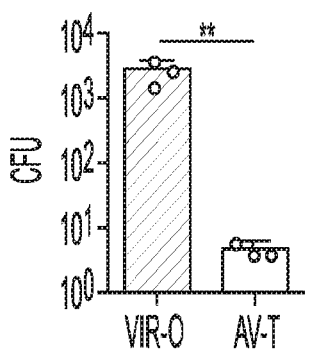
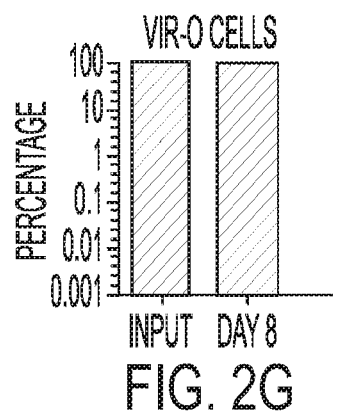
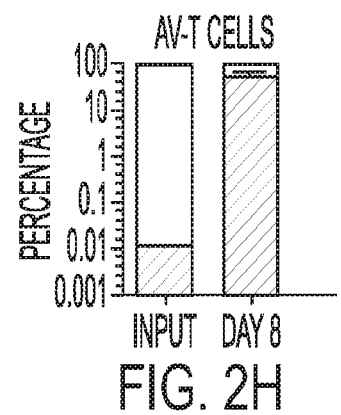
FIG. 2F   FIG. 2G   FIG. 2H

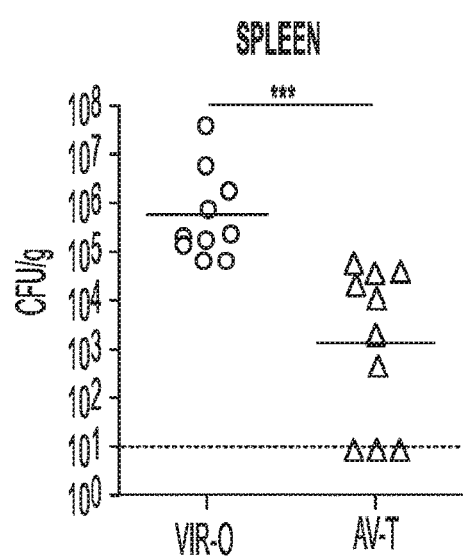 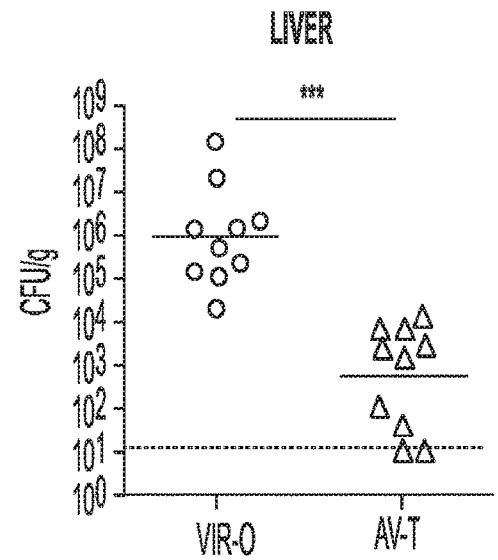
FIG. 7A  FIG. 7B
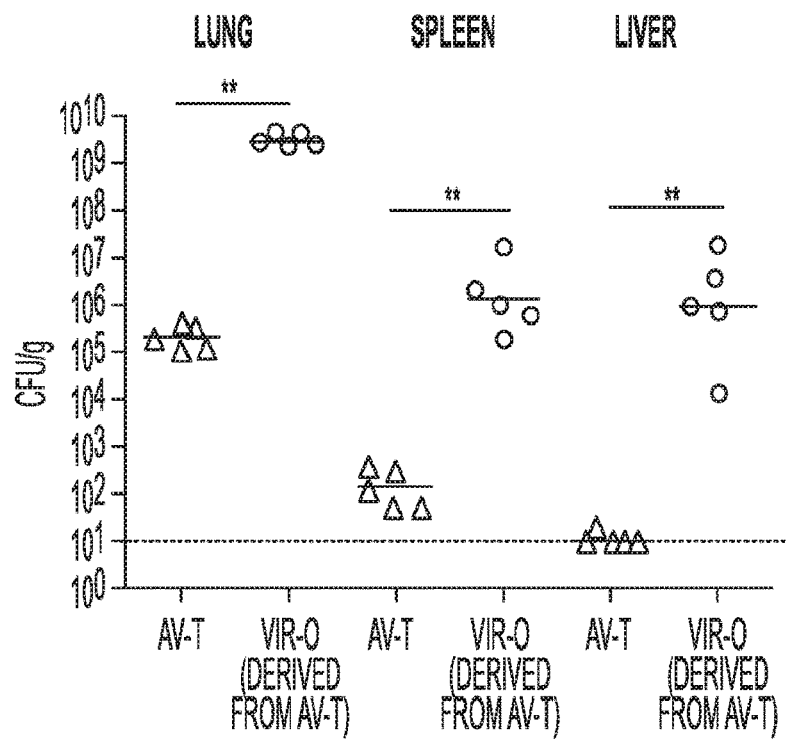
FIG. 8

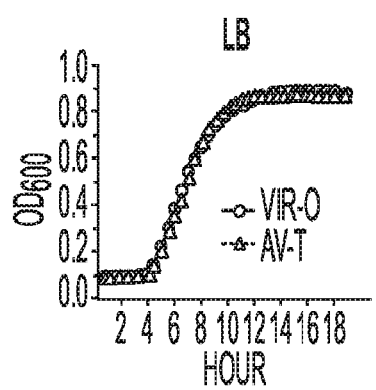 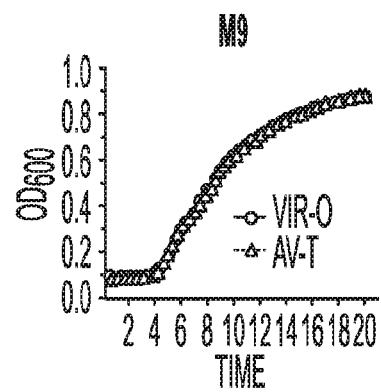 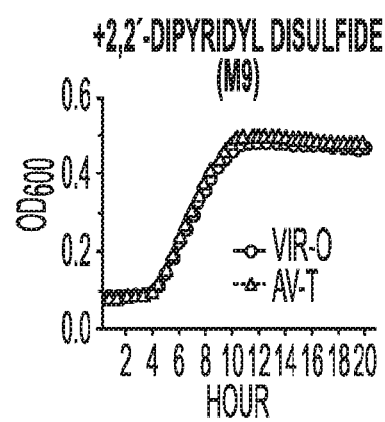
FIG. 9A  FIG. 9B  FIG. 9C
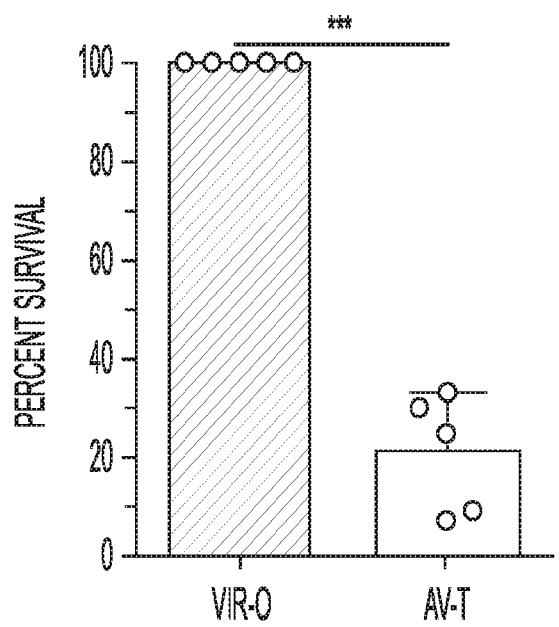
FIG. 10

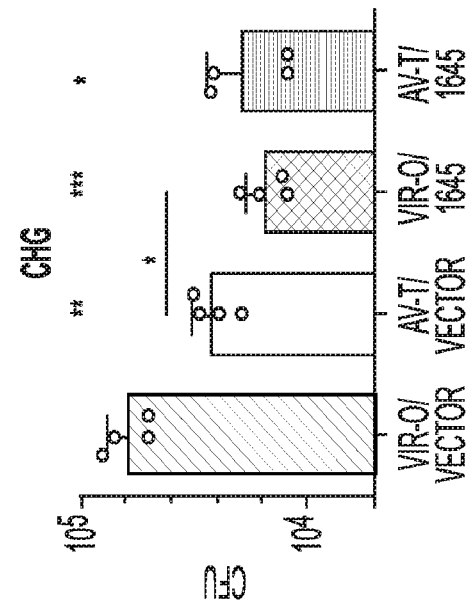
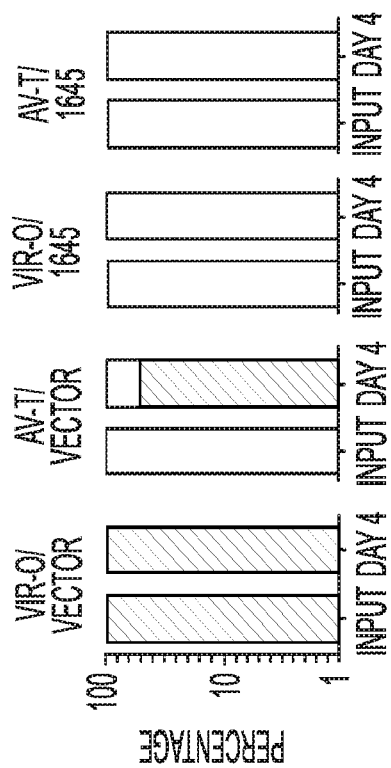
FIG. 14A
FIG. 14B
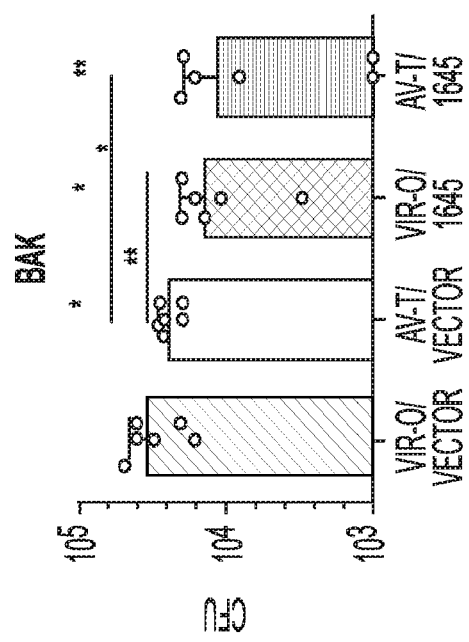
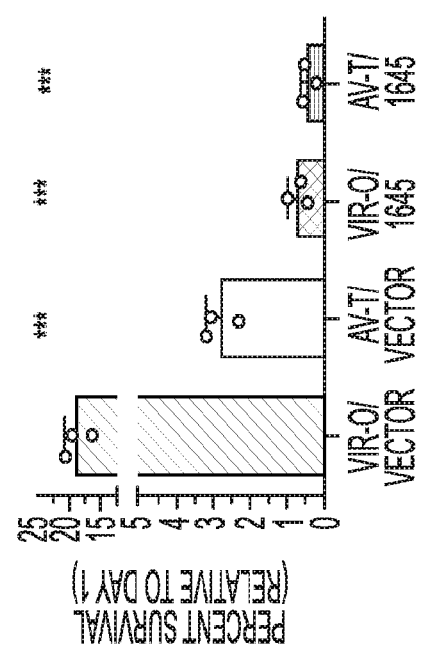
FIG. 14C
FIG. 14D

```
                          SEQUENCE LISTING

<160> NUMBER OF SEQ ID NOS: 13

<210> SEQ ID NO 1
<211> LENGTH: 183
<212> TYPE: PRT
<213> ORGANISM: Acinetobacter baumannii

<400> SEQUENCE: 1

Pro Asn Leu Glu Ala Ser Phe Arg Ala Leu Arg Val Leu His Thr Ala
1               5                   10                  15

Arg Asp Leu Phe Lys Gln Tyr Gly Phe His Lys Val Gly Val Asp Arg
            20                  25                  30

Ile Ile Ala Glu Ser Lys Ile Thr Lys Ala Thr Phe Tyr Asn Tyr Phe
        35                  40                  45

His Ser Lys Glu Arg Leu Ile Glu Met Cys Leu Thr Phe Gln Lys Asp
    50                  55                  60

Gly Leu Lys Glu Glu Val Phe Ser Ile Ile Tyr Ser Tyr Arg Glu Leu
65                  70                  75                  80

Met Val Phe Asp Lys Leu Lys Lys Ile Phe Phe Leu His Ala Asn Leu
                85                  90                  95

Glu Gly Leu Tyr Arg Leu Pro Leu Gln Ala Ile Phe Glu Ile Glu Lys
            100                 105                 110

Phe Tyr Pro Thr Ala Tyr Lys Val Val Val Asp Tyr Arg Asn Trp Leu
        115                 120                 125

Val Thr Gln Ile His Gln Leu Leu Leu Thr Ile Lys Ala Thr Ala Thr
    130                 135                 140

Leu Glu Asp Ala Tyr Met Phe Leu Phe Val Ile Asp Gly Ala Met Val
145                 150                 155                 160

Gln Leu Leu Ser Lys Asp Arg Ile Asp Glu Arg Asp Lys Leu Leu Asp
                165                 170                 175

Tyr Phe Leu Ile Ile Leu Ser
            180

<210> SEQ ID NO 2
<211> LENGTH: 183
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is any amino acid
<220> FEATURE:
<221> NAME/KEY: MISC_FEATURE
<222> LOCATION: (6)..(6)
<223> OTHER INFORMATION: Xaa at position 6 is any amino acid
<220> FEATURE:
<221> NAME/KEY: MISC_FEATURE
<222> LOCATION: (12)..(12)
<223> OTHER INFORMATION: Xaa at position 12 is any amino acid
<220> FEATURE:
<221> NAME/KEY: MISC_FEATURE
<222> LOCATION: (21)..(21)
<223> OTHER INFORMATION: Xaa at position 21 is any amino acid
<220> FEATURE:
<221> NAME/KEY: MISC_FEATURE
<222> LOCATION: (64)..(64)
<223> OTHER INFORMATION: Xaa at position 64 is any amino acid
<220> FEATURE:
<221> NAME/KEY: MISC_FEATURE
<222> LOCATION: (78)..(78)
```

<223> OTHER INFORMATION: Xaa at position 78 is any amino acid
<220> FEATURE:
<221> NAME/KEY: MISC_FEATURE
<222> LOCATION: (89)..(89)
<223> OTHER INFORMATION: Xaa at position 89 is any amino acid
<220> FEATURE:
<221> NAME/KEY: MISC_FEATURE
<222> LOCATION: (97)..(97)
<223> OTHER INFORMATION: Xaa at position 97 is any amino acid
<220> FEATURE:
<221> NAME/KEY: MISC_FEATURE
<222> LOCATION: (104)..(104)
<223> OTHER INFORMATION: Xaa at position 104 is any amino acid
<220> FEATURE:
<221> NAME/KEY: MISC_FEATURE
<222> LOCATION: (117)..(117)
<223> OTHER INFORMATION: Xaa at position 117 is any amino acid
<220> FEATURE:
<221> NAME/KEY: MISC_FEATURE
<222> LOCATION: (130)..(130)
<223> OTHER INFORMATION: Xaa at position 130 is any amino acid
<220> FEATURE:
<221> NAME/KEY: MISC_FEATURE
<222> LOCATION: (142)..(142)
<223> OTHER INFORMATION: Xaa at position 142 is any amino acid
<220> FEATURE:
<221> NAME/KEY: MISC_FEATURE
<222> LOCATION: (144)..(144)
<223> OTHER INFORMATION: Xaa at position 144 is any amino acid
<220> FEATURE:
<221> NAME/KEY: MISC_FEATURE
<222> LOCATION: (148)..(148)
<223> OTHER INFORMATION: Xaa at position 148 is any amino acid
<220> FEATURE:
<221> NAME/KEY: MISC_FEATURE
<222> LOCATION: (180)..(180)
<223> OTHER INFORMATION: Xaa at position 180 is any amino acid
<220> FEATURE:
<221> NAME/KEY: MISC_FEATURE
<222> LOCATION: (181)..(181)
<223> OTHER INFORMATION: Xaa at position 181 is any amino acid
<220> FEATURE:
<221> NAME/KEY: MISC_FEATURE
<222> LOCATION: (182)..(182)
<223> OTHER INFORMATION: Xaa at position 182 is any amino acid

<400> SEQUENCE: 2

Pro Xaa Leu Glu Ala Xaa Phe Arg Ala Leu Arg Xaa Leu His Thr Ala
1               5                   10                  15

Arg Asp Leu Phe Xaa Gln Tyr Gly Phe His Lys Val Gly Val Asp Arg
            20                  25                  30

Ile Ile Ala Glu Ser Lys Ile Thr Lys Ala Thr Phe Tyr Asn Tyr Phe
        35                  40                  45

His Ser Lys Glu Arg Leu Ile Glu Met Cys Leu Thr Phe Gln Lys Xaa
50                  55                  60

Gly Leu Lys Glu Glu Val Phe Ser Ile Ile Tyr Ser Tyr Xaa Glu Leu
65                  70                  75                  80

Met Val Phe Asp Lys Leu Lys Lys Xaa Phe Phe Leu His Ala Asn Leu
                85                  90                  95

Xaa Gly Leu Tyr Arg Leu Pro Xaa Gln Ala Ile Phe Glu Ile Glu Lys
            100                 105                 110

Phe Tyr Pro Thr Xaa Tyr Lys Val Val Val Asp Tyr Arg Asn Trp Leu
        115                 120                 125

Val Xaa Gln Ile His Gln Leu Leu Leu Thr Ile Lys Ala Xaa Ala Xaa
    130                 135                 140

Leu Glu Asp Xaa Tyr Met Phe Leu Phe Val Ile Asp Gly Ala Met Val
145                 150                 155                 160

Gln Leu Leu Ser Lys Asp Arg Ile Asp Glu Arg Asp Lys Leu Leu Asp

```
                    165                 170                 175

Tyr Phe Leu Xaa Xaa Xaa Ser
        180

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
gagtgacggc atgtctatct                                             20

<210> SEQ ID NO 4
<211> LENGTH: 25
<212> TYPE: DNA
<213> ORGANISM: Artificial Sequence
<220> FEATURE:
<223> OTHER INFORMATION: Synthetic construct

<400> SEQUENCE: 4
cttatagcca taagtggtaa ttgag                                       25

<210> SEQ ID NO 5
<211> LENGTH: 33
<212> TYPE: DNA
<213> ORGANISM: Artificial Sequence
<220> FEATURE:
<223> OTHER INFORMATION: Synthetic construct

<400> SEQUENCE: 5
aaaaaggatc cctacagacc ttaaataacg gtg                              33

<210> SEQ ID NO 6
<211> LENGTH: 30
<212> TYPE: DNA
<213> ORGANISM: Artificial Sequence
<220> FEATURE:
<223> OTHER INFORMATION: Synthetic construct

<400> SEQUENCE: 6
aaaaaggatc ctggtcaaac tttacgtggt                                  30

<210> SEQ ID NO 7
<211> LENGTH: 21
<212> TYPE: DNA
<213> ORGANISM: Artificial Sequence
<220> FEATURE:
<223> OTHER INFORMATION: Synthetic construct

<400> SEQUENCE: 7
tgctctaaat gaagcttcta a                                           21

<210> SEQ ID NO 8
<211> LENGTH: 30
<212> TYPE: DNA
<213> ORGANISM: Artificial Sequence
<220> FEATURE:
<223> OTHER INFORMATION: Synthetic construct

<400> SEQUENCE: 8
ataatactgt cctagattaa aaataaaagc                                  30

<210> SEQ ID NO 9
```

```
<211> LENGTH: 6
<212> TYPE: PRT
<213> ORGANISM: Artificial Sequence
<220> FEATURE:
<223> OTHER INFORMATION: Synthetic construct

<400> SEQUENCE: 9

Gly Gly Gly Gly Gly Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic construct

<400> SEQUENCE: 10

Gly Gly Gly Gly Thr
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic construct

<400> SEQUENCE: 11

Gly Gly Gly Pro Pro Pro
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic construct

<400> SEQUENCE: 12

Gly Gly Gly Ala Pro Pro Pro
1               5

<210> SEQ ID NO 13
<211> LENGTH: 36
<212> TYPE: PRT
<213> ORGANISM: Acinetobacter baumannii

<400> SEQUENCE: 13

Phe His Lys Val Gly Val Asp Arg Ile Ile Ala Glu Ser Lys Ile Thr
1               5                   10                  15

Lys Ala Thr Phe Tyr Asn Tyr Phe His Ser Lys Glu Arg Leu Ile Glu
            20                  25                  30

Met Cys Leu Thr
            35
```

BACTERIAL PROTEIN COMPOSITIONS AND USES THEREOF

CROSS REFERENCE TO RELATED PATENT APPLICATIONS

This application claims the benefit of priority under 35 U.S.C. § 371 of International Application No. PCT/US2018/051768, filed on Sep. 19, 2018, which claims priority to U.S. Provisional Application No. 62/561,199, filed Sep. 20, 2017. The content of these earlier filed applications is hereby incorporated by reference herein in its entirety.

STATEMENT REGARDING FEDERALLY FUNDED RESEARCH

This invention was made with government support under Grant No. AI115183, awarded by the National Institutes of Health, and by the U.S. Dept. of Veterans Affairs to Emory University under VA ID 2017-447. The government has certain rights in the invention.

INCORPORATION OF THE SEQUENCE LISTING

The present application contains a sequence listing that is submitted via EFS-Web concurrent with the filing of this application, containing the file name "37759_0087U2_SL.text" which is 8,192 bytes in size, created on Mar. 11, 2020, and is herein incorporated by reference in its entirety pursuant to 37 C.F.R. § 1.52(e)(5).

BACKGROUND

Antibiotic resistant infections lead to 700,000 deaths per year worldwide (O'Neill, J., Review on Antimicrobial Resistance: Tackling drug resistant infections globally. London (2014)). The roles of phenotypically diverse subpopulations of clonal bacteria in the progression of diseases are unclear. *Acinetobacter baumannii* has become a major healthcare threat worldwide, responsible for both hospital and community acquired infections (Bergogne-Berezin, E. & Towner, K. J. Clinical microbiology reviews 9, 148-165 (1996); Antunes, L. C., Visca, P. & Towner, K. J. Pathogens and disease 71, 292-301 (2014); Dijkshoorn, L., Nemec, A. & Seifert, H. Nature reviews. Microbiology 5, 939-951 (2007); Joly-Guillou, M. L. Clinical microbiology and infection: the official publication of the European Society of Clinical Microbiology and Infectious Diseases 11, 868-873 (2005); and Murray, C. K. & Hospenthal, D. R. Critical care clinics 24, 237-248, vii, (2008)). These infections have become increasingly virulent (Charnot-Katsikas, A. et al. Journal of clinical microbiology 47, 258-263 (2009); Guerrero, D. M. et al. Surgical infections 11, 49-57 (2010); Lowman, W., Kalk, T., Menezes, C. N., John, M. A. & Grobusch, M. P. Journal of medical microbiology 57, 676-678 (2008); and Telang, N. V., Satpute, M. G., Dhakephalkar, P. K., Niphadkar, K. B. & Joshi, S. G. Indian journal of pathology & microbiology 54, 180-182, (2011)) and exceedingly difficult to treat due to high levels of antibiotic resistance (63% of isolates in the US are multidrug-resistant, and some isolates are even pan-resistant) (Boucher, H. W. et al. Clinical infectious diseases: an official publication of the Infectious Diseases Society of America 48, 1-12 (2009); Doi, Y., Husain, S., Potoski, B. A., McCurry, K. R. & Paterson, D. L. Emerging infectious diseases 15, 980-982 (2009); Gottig, S. et al. The Journal of antimicrobial chemotherapy 69, 2578-2579 (2014); Lei, J. et al. American journal of infection control (2016); and Park, Y. K. et al. Emerging infectious diseases 15, 1325-1327 (2009)). *A. baumannii* is also notoriously difficult to eradicate in hospital settings (Bergogne-Berezin, E. & Towner, K. J. Clinical microbiology reviews 9, 148-165 (1996) and Lei, J. et al. American journal of infection control (2016)) and contamination of intensive care wards is a frequent problem (Murray, C. K. & Hospenthal, D. R. Critical care clinics 24, 237-248, vii (2008); Maragakis, L. L. & Perl, T. M. Clinical infectious diseases: an official publication of the Infectious Diseases Society of America 46, 1254-1263 (2008); and Villegas, M. V. & Hartstein, A. I. Infection control and hospital epidemiology 24, 284-295 (2003)). The remarkable ability of *A. baumannii* to persist in this environment is due to both its intrinsic resistance to commonly used disinfectants and its ability to survive long periods of desiccation (Fernandez-Cuenca, F. et al. The Journal of antimicrobial chemotherapy 70, 3222-3229 (2015); Jawad, A., Seifert, H., Snelling, A. M., Heritage, J. & Hawkey, P. M. Journal of clinical microbiology 36, 1938-1941 (1998); Hassan, K. A. et al. Proceedings of the National Academy of Sciences of the United States of America 110, (2013); and Brooks, S. E., Walczak, M. A., Hameed, R. & Coonan, P. Infection control and hospital epidemiology 23, 692-695 (2002)). However, the molecular mechanisms controlling virulence, resistance to disinfectants, and desiccation tolerance remain poorly understood.

SUMMARY

Disclosed herein is an attenuated *Acinetobacter baumannii* and variants thereof.

Disclosed herein is an attenuated *Acinetobacter baumannii* comprising an expression vector comprising a nucleic acid encoding the ABUW_1645 protein (SEQ ID NO: 1) or a variant thereof.

Disclosed herein is an attenuated *Acinetobacter baumannii* comprising an expression vector comprising a nucleic acid encoding the ABUW_1645 protein, PNLEASFRALRVLHTARDLFKQYGFHKVGVDRII-AESKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof.

Disclosed herein is an attenuated *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant has greater than 70%, 80%, 90%, 95%, 96%, 97%, 98% or 99% identity or similarity to SEQ ID NO: 1.

Disclosed herein is an attenuated *Acinetobacter baumannii* or a variant thereof, wherein the variant comprises a nucleic acid encoding the amino acid sequence pX$^1$leaX$^2$fralrX$^3$lhtardlfX$^4$qygfhkvgvdriiaeskitkatf ynyfhsk-erliemcltfqkX$^5$glkeevfsiiysyX$^6$ elmvfdklkkX$^7$fflhanlX$^8$glyrlpX$^9$qaifeiekfyptX$^{10}$ykvvvdyrn wlvX$^{11}$qihqllltikaX$^{12}$aX$^{13}$ledX$^{14}$ ymflfvidgamvqllskdriderdklldyflX$^{15}$X$^{16}$X$^{17}$s (SEQ ID NO: 2), wherein X$^1$ to X$^{17}$ are each individually and independently any amino acid or a conserved amino acid compared to the corresponding amino acid in SEQ ID NO: 1.

Disclosed herein is an attenuated *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises a nucleic acid encoding the amino acid sequence pX$^1$leaX$^2$fralrX$^3$lhtardlfX$^4$qygfhkvgvdriiaeskitkatfynyfhskerliemcltfqkX$^5$glkeevfsiiys yX$^6$elmvfdklkkX$^7$fflhanlX$^8$glyrlpX$^9$qaifeiekfyptX$^{10}$kvvvdyrnwlvX$^{11}$qihqllltikaX$^{12}$aX$^{13}$ledX$^{14}$ymflfvidgamvqll skdriderdklldyflX$^{15}$X$^{16}$X$^{17}$s (SEQ ID NO: 2), wherein X$^1$ to X$^{17}$ are each individually and independently any amino acid or a conserved amino acid compared to the corresponding amino acid in SEQ ID NO: 1.

Disclosed herein is an attenuated *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant has greater than 70%, 80%, 90%, 95%, 96%, 97%, 98% or 99% identity or similarity to SEQ ID NO: 1.

Disclosed herein is an attenuated *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1.

Disclosed herein are pharmaceutical compositions comprising an attenuated *Acinetobacter baumannii* comprising an expression vector comprising a nucleic acid encoding the ABUW_1645 protein, PNLEASFRALRVLH-TARDLFKQYGFHKVGVDRIIAE SKITKATFYNYFHS-KERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof; and a pharmaceutically acceptable excipient.

Disclosed herein are pharmaceutical compositions comprising an attenuated *Acinetobacter baumannii* comprising an expression vector comprising a nucleic acid encoding the ABUW_1645 protein, PNLEASFRALRVLH-TARDLFKQYGFHKVGVDRIIAE SKITKATFYNYFHS-KERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant has greater than 70%, 80%, 90%, 95%, 96%, 97%, 98% or 99% identity or similarity to SEQ ID NO:1; and a pharmaceutically acceptable excipient.

Disclosed herein are pharmaceutical compositions comprising an attenuated *Acinetobacter baumannii* comprising an expression vector comprising a nucleic acid encoding the ABUW_1645 protein, PNLEASFRALRVLH-TARDLFKQYGFHKVGVDRIIAE SKITKATFYNYFHS-KERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises a nucleic acid encoding the amino acid sequence pX$^1$leaX$^2$fralrX$^3$lhtardlfX$^4$qygfhkvgvdriiaeskitkatfynyfhskerliemcltfqkX$^5$glkeevfsiiysyX$^6$elmvfdklkkX$^7$fflhanlX$^8$glyrlpX$^9$qaifeiekfyptX$^{10}$ykvvvdyrnwlvX$^{11}$qihqllltikaX$^{12}$aX$^{13}$led X$^{14}$ymflfvidgamvqllskdriderdklldyflX$^{15}$X$^{16}$X$^{17}$s (SEQ ID NO: 2), wherein X$^1$ to X$^{17}$ are each individually and independently any amino acid or a conserved amino acid compared to the corresponding amino acid in SEQ ID NO: 1; and a pharmaceutically acceptable excipient.

Disclosed herein are pharmaceutical compositions comprising an attenuated *Acinetobacter baumannii* comprising an expression vector comprising a nucleic acid encoding the ABUW_1645 protein, PNLEASFRALRVLH-TARDLFKQYGFHKVGVDRIIAE SKITKATFYNYFHS-KERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1; and a pharmaceutically acceptable excipient.

Disclosed herein are methods of vaccinating against *Acinetobacter baumannii* comprising administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof to a subject in need thereof.

Disclosed herein are methods of vaccinating against *Acinetobacter baumannii* comprising administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant has greater than 70%, 80%, 90%, 95%, 96%, 97%, 98% or 99% identity or similarity to SEQ ID NO: 1; to a subject in need thereof.

Disclosed herein are methods of vaccinating against *Acinetobacter baumannii* comprising administering an *Acinetobacter baumannii comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises a nucleic acid encoding the amino acid sequence pX$^1$leaX$^2$fralrX$^3$lhtardlfX$^4$qygfhkvgvdriiaeskitkatfynyfhskerliemcltfqkX$^5$glkeevfsiiysyX$^6$elmvfdklkkX$^7$fflhanlX$^8$glyrlpX$^9$qaifeiekfyptX$^{10}$ykvvvdyrnwlvX$^{11}$qihqllltikaX$^{12}$aX$^{13}$ledX$^{14}$ymflfvidgamvqllskdriderdklldyflX$^{15}$X$^{16}$X$^{17}$s (SEQ ID NO: 2), wherein X$^1$ to X$^{17}$ are each individually and independently any amino acid or a conserved amino acid compared to the corresponding amino acid in SEQ ID NO: 1 to a subject in need thereof.

Disclosed herein are methods of vaccinating against *Acinetobacter baumannii* comprising administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1 to a subject in need thereof.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof to a subject in need thereof.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant has greater than 70%, 80%, 90%, 95%, 96%, 97%, 98% or 99% identity or similarity to SEQ ID NO: 1; to a subject in need thereof.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises a nucleic acid encoding the amino acid sequence pX$^1$leaX$^2$fralrX$^3$lhtardlfX$^4$qygfhkvgvdriiaeskitkatfynyfhskerliemcltfqkX$^5$glkeevfsiiysyX$^6$elmvfdklkkX$^7$fflhanlX$^8$glyrlpX$^9$qaifeiekfyptX$^{10}$ykvvvdyrnwlvX$^{11}$qihqllltikaX$^{12}$aX$^{13}$ledX$^{14}$ymflfvidgamvqllskdriderdklldyflX$^{15}$X$^{16}$X$^{17}$s (SEQ ID NO: 2), wherein X$^1$ to X$^{17}$ are each individually and independently any amino acid or a conserved amino acid compared to the corresponding amino acid in SEQ ID NO: 1 to a subject in need thereof.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1 to a subject in need thereof.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof to a subject in need thereof, wherein the administering of the *Acinetobacter baumannii* is in combination with one or more an antibiotics or antimicrobial agents.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant has greater than 70%, 80%, 90%, 95%, 96%, 97%, 98% or 99% identity or similarity to SEQ ID NO: 1; to a subject in need thereof, wherein the administering of the *Acinetobacter baumannii* is in combination with one or more an antibiotics or antimicrobial agents.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises a nucleic acid encoding the amino acid sequence pX$^1$leaX$^2$fralrX$^3$lhtardlfX$^4$ qygfhkvgvdriiaeskitkatfynyfhskerliemcltfqkX$^5$glkeevfsiiys yX$^6$elmvfdklkkX$^7$fflhanlX$^8$glyrlpX$^9$qaifeiekfyptX$^{10}$ ykvvvdyrnwlvX$^{11}$qihqllltikaX$^{12}$aX$^{13}$ledX$^{14}$ymflfvidgamvq llskdriderdklldyflX$^{15}$X$^{16}$X$^{17}$s (SEQ ID NO: 2), wherein X$^1$ to X$^{17}$ are each individually and independently any amino acid or a conserved amino acid compared to the corresponding amino acid in SEQ ID NO: 1 to a subject in need thereof, wherein the administering of the *Acinetobacter baumannii* is in combination with one or more an antibiotics or antimicrobial agents.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1 to a subject in need thereof, wherein the administering of the *Acinetobacter baumannii* is in combination with one or more an antibiotics or antimicrobial agents.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof to a subject in need thereof, wherein the administering of the *Acinetobacter baumannii* is in combination with one or more an antibiotics or antimicrobial agents, wherein the one or more antibiotics is imipenem, meropenem, or colistin.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant has greater than 70%, 80%, 90%, 95%, 96%, 97%, 98% or 99% identity or similarity to SEQ ID NO: 1; to a subject in need thereof, wherein the administering of the *Acinetobacter baumannii* is in combination with one or more an antibiotics or antimicrobial agents, wherein the one or more antibiotics is imipenem, meropenem, or colistin.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRII-AESKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises a nucleic acid encoding the amino acid sequence pX$^1$leaX$^2$fralrX$^3$lhtardlfX$^4$ qygfhkvgvdriiaeskitkatfynyfhskerliemcltfqkX$^5$glkeevfsiiys yX$^6$ elmvfdklkkX$^7$fflhanlX$^8$glyrlpX$^9$qaifeiekfyptX$^{10}$ ykvvvdyrnwlvX$^{11}$qihqllltikaX$^{12}$aX$^{13}$ledX$^{14}$ ymflfvidgamvqllskdriderdklldyflX$^{15}$X$^{16}$X$^{17}$s (SEQ ID NO: 2), wherein X$^1$ to X$^{17}$ are each individually and independently any amino acid or a conserved amino acid compared to the corresponding amino acid in SEQ ID NO: 1 to a subject in need thereof, wherein the administering of the *Acinetobacter baumannii* is in combination with one or more an antibiotics or antimicrobial agents, wherein the one or more antibiotics is imipenem, meropenem, or colistin.

Disclosed herein are method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1 to a subject in need thereof, wherein the administering of the *Acinetobacter baumannii* is in combination with one or more an antibiotics or antimicrobial agents, wherein the one or more antibiotics is imipenem, meropenem, or colistin.

Disclosed herein are methods of treating or preventing colonization, infection, or disease by an *Acinetobacter baumannii* microbe, the method comprising administering a clinically effective dose of the attenuated *Acinetobacter baumannii* to a subject in need thereof, wherein the attenuated *Acinetobacter baumannii* comprises an expression vector expressing the ABUW_1645 protein, PNLEASFRALRVLHTARDLFKQYGFHKVGVDRII AESKITKATFYNYFHSKERLIEMCLTFQKDGL-KEEVFSIIYSYRELMVFDKLKKIF FLHANLEG-LYRLPLQAIFEIEKFYPT-AYKVVVDYRNWLVTQIHQLLLTIKATATL EDAYMFLFVIDGAMVQLLSKDRIDERDKLLDYF-LIILS (SEQ ID NO: 1), or a variant thereof.

Disclosed herein are methods of treating or preventing colonization, infection, or disease by an *Acinetobacter baumannii* microbe, the method comprising administering a clinically effective dose of the attenuated *Acinetobacter baumannii* to a subject in need thereof, wherein the attenuated *Acinetobacter baumannii* comprises an expression vector expressing the ABUW_1645 protein, PNLEASFRALRVLHTARDLFKQYGFHKVGVDRII AESKITKATFYNYFHSKERLIEMCLTFQKDGL-KEEVFSIIYSYRELMVFDKLKKIF FLHANLEG-LYRLPLQAIFEIEKFYPT-AYKVVVDYRNWLVTQIHQLLLTIKATATL EDAYMFLFVIDGAMVQLLSKDRIDERDKLLDYF-LIILS (SEQ ID NO: 1), or a variant thereof, wherein the attenuated *Acinetobacter baumannii* is administered before the administration of an antimicrobial agent.

Disclosed herein are methods of treating or preventing colonization, infection, or disease by an *Acinetobacter baumannii* microbe, the method comprising administering a clinically effective dose of the attenuated *Acinetobacter baumannii* to a subject in need thereof, wherein the attenuated *Acinetobacter baumannii* comprises an expression vector expressing the ABUW_1645 protein, PNLEASFRALRVLHTARDLFKQYGFHKVGVDRII AESKITKATFYNYFHSKERLIEMCLTFQKDGL-KEEVFSIIYSYRELMVFDKLKKIF FLHANLEG-LYRLPLQAIFEIEKFYPT-AYKVVVDYRNWLVTQIHQLLLTIKATATL EDAYMFLFVIDGAMVQLLSKDRIDERDKLLDYF-LIILS (SEQ ID NO: 1), or a variant thereof, wherein the attenuated *Acinetobacter baumannii* is administered orally.

Disclosed herein are methods of treating or preventing colonization, infection, or disease by an *Acinetobacter baumannii* microbe, the method comprising administering a clinically effective dose of the attenuated *Acinetobacter baumannii* to a subject in need thereof, wherein the attenuated *Acinetobacter baumannii* comprises an expression vector expressing the ABUW_1645 protein, PNLEASFRALRVLHTARDLFKQYGFHKVGVDRII AESKITKATFYNYFHSKERLIEMCLTFQKDGL-KEEVFSIIYSYRELMVFDKLKKIF FLHANLEG-LYRLPLQAIFEIEKFYPT-AYKVVVDYRNWLVTQIHQLLLTIKATATL EDAYMFLFVIDGAMVQLLSKDRIDERDKLLDYF-LIILS (SEQ ID NO: 1), or a variant thereof, wherein the attenuated *Acinetobacter baumannii* is administered as a live attenuated *Acinetobacter baumannii*.

Disclosed herein is an attenuated *Acinetobacter baumannii* comprising an expression vector comprising a nucleic acid encoding an ABUW_1645 variant.

Disclosed herein is an attenuated *Acinetobacter baumannii* comprising an expression vector comprising a nucleic acid encoding an ABUW_1645 variant, wherein the ABUW_1645 variant is greater than 70%, 80%, 90%, 95%, 96%, 97%, 98% or 99% identity or similarity to SEQ ID NO: 1.

Disclosed herein is an attenuated *Acinetobacter baumannii* comprising an expression vector comprising a nucleic acid encoding an ABUW_1645 variant, wherein the ABUW_1645 variant is less than 70%, 80%, 90%, 95%, 96%, 97%, 98% or 99% identity or similarity to SEQ ID NO: 1

Disclosed herein is an attenuated *Acinetobacter baumannii* comprising an expression vector comprising a nucleic acid encoding an ABUW_1645 variant, wherein the ABUW_1645 variant comprises SEQ ID NO: 13.

Disclosed herein is an attenuated *Acinetobacter baumannii* comprising an expression vector comprising a nucleic acid encoding an ABUW_1645 variant, wherein the ABUW_1645 variant comprises a sequence that is 70%, 80%, or 90% identical to SEQ ID NO: 13.

Disclosed herein is an attenuated *Acinetobacter baumannii* comprising an expression vector comprising a nucleic acid encoding an ABUW_1645 variant, wherein the ABUW_1645 variant comprises a sequence that is less than 70% identical or similar to SEQ ID NO: 1 and has a sequence that is greater than 70% identical or similar to SEQ ID NO: 13.

Disclosed herein is an attenuated *Acinetobacter baumannii* comprising an expression vector comprising a nucleic acid encoding an ABUW_1645 variant, wherein the ABUW_1645 variant comprises a sequence that is greater than 70% identical or similar to SEQ ID NO: 1 and has a sequence that is greater than 70% identical or similar to SEQ ID NO: 13.

Disclosed herein is an attenuated *Acinetobacter baumannii* comprising an expression vector comprising a nucleic acid encoding an ABUW_1645 variant, wherein the variant has a less than 70% identity or similarity to SEQ ID NO: 1 and has a greater than 70% identity or similarity to SEQ ID NO: 13.

Disclosed herein is an attenuated *Acinetobacter baumannii* comprising an expression vector comprising a nucleic acid encoding an ABUW_1645 variant, wherein the variant has a greater than 70% identity or similarity to SEQ ID NO: 1 and has a greater than 70% identity or similarity to SEQ ID NO: 13.

Disclosed herein are methods of treating or preventing colonization, infection, or disease by a *Acinetobacter baumannii* microbe comprising administering a clinically effective dose of an attenuated *Acinetobacter baumannii* to a subject in need thereof, wherein the attenuated *Acinetobacter baumannii* comprises an expression vector expressing a variant, wherein the variant has a less than 70% identity or similarity to SEQ ID NO: 1 and has a greater than 70% identity or similarity to SEQ ID NO: 13.

Disclosed herein are methods of treating or preventing colonization, infection, or disease by a *Acinetobacter baumannii* microbe comprising administering a clinically effective dose of an attenuated *Acinetobacter baumannii* to a subject in need thereof, wherein the attenuated *Acinetobacter baumannii* comprises an expression vector expressing a variant, wherein the variant has a greater than 70% identity or similarity to SEQ ID NO: 1 and has a greater than 70% identity or similarity to SEQ ID NO: 13.

Other features and advantages of the present compositions and methods are illustrated in the description below, the drawings, and the claims.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 1A-H shows a highly virulent opaque (VIR-O) population is responsible for causing disease during in vivo pulmonary infection of mice. FIG. 1A shows representative *A. baumannii* strain AB5075 wild-type virulent opaque (VIR-O) and avirulent translucent (AV-T) colonies. FIG. 1B shows strains that were stained for capsule with ruthenium red and imaged by transmission electron microscopy. Representative images are shown for each strain. Scale bars in each image represent 100 nanometers. FIG. 1C shows that capsule abundance of the indicated strains was determined by capsule extraction and quantitation on SDS-PAGE gels stained with Alcian blue. Values were obtained from three biological replicates and error bars represent standard deviation of the mean. p-values (p<0.005; *p<0.0005) were determined using one-way ANOVA. FIG. 1D shows mice infected with a 1:1 mixture of VIR-O (red) and AV-T (blue) strains (n=5/group). FIG. 1E shows mice infected with VIR-O and AV-T (n=5/group). Bacteria recovered from the (FIG. 1F) VIR-O and (FIG. 1G) AV-T-infected lungs were assessed for the percentage of VIR-O and AV-T cells present, respectively. FIG. 1H shows survival of mice infected with VIR-O and AV-T (n=5/group). This experiment was repeated 3 times. Error bars represent standard deviation of the mean in (d, f and g); Error bars represent geometric mean and significance was determined using a two-tailed Mann-Whitney test (***p<0.0005) in (E).

FIGS. 2A-H show the host antimicrobial, hospital disinfectant and desiccation-resistant VIR-O cells selected during in vivo infection. FIG. 2A shows VIR-O (red) or AV-T (blue) were treated with $H_2O_2$, CRAMP or lysozyme, and percent survival calculated relative to VIR-O. The reported values represent the mean of three replicates with standard deviations. Repeated experiments gave similar results. FIG. 2B shows wild-type (WT, black) or triple knockout (TKO; red) mice lacking the gp91 subunit of the NADPH oxidase, lysozyme and CRAMP were infected with AV-T (n=4 to 8/group). FIGS. 2C-E show VIR-O or AV-T was treated with the indicated amounts of disinfectants: (FIG. 2C) benzethonium chloride (BZT) 0.01%, (FIG. 1D) benzalkonium chloride (BAK) 0.004% and (FIG. 2E) chlorhexidine gluconate (CHG) 0.008%, and percent survival relative to VIR-O was calculated. Presented data were pooled from three separate experiments and a total of 5 replicates were used for (FIG. 2C), 6 replicates for (FIG. 2D) and 7 replicates for (FIG. 2E). FIGS. F-H show VIR-O and AV-T survival after desiccation. FIG. 2F show bacteria were rehydrated and plated on day 8 of desiccation to determine viability. Values represent the mean of three replicates. Recovered bacteria from the (FIG. 2G) VIR-O cells and (FIG. 2H) AV-T cells were assessed for the percentage of VIR-O and AV-T cells present. Error bars represent standard deviation of the mean and Student's two-tailed t-test (p<0.005; *p<0.0005) in (A) and (C-H); Error bars represent geometric mean and a two-tailed Mann-Whitney test was to determine significance (***p<0.0005) in (FIG. 2B).

FIGS. 3A-H show ABUW_1645 is a global regulator in mediating phenotypic switching, virulence and resistance to host defenses. FIG. 3A shows representative colonies of VIR-O or AV-T cells overexpressing ABUW_1645 or with empty vector. FIG. 3B shows VIR-O/vector (red) and VIR-O/1645 (green) treated with lysozyme, $H_2O_2$ or CRAMP, and percent survival was calculated relative to VIR-O/vector. The reported values represent the mean of three independent replicates with standard deviations. Repeated experiments gave similar results. FIGS. 3C, D show mice infected with VIR-O/vector (red), AV-T/vector (blue), VIR-O/1645 (green) or AV-T/1645 (gold) strains (10 mice/group). At 24 hours post-infection, lungs were harvested and plated for colony forming units (FIG. 3D) and assessed for the percentage of VIR-O and AV-T cells present (FIG. 3C). FIG. 3E shows the survival of mice infected with VIR-O/vector and VIR-O/1645 (n=5/group). This experiment was repeated two times with identical results. FIG. 3F shows the survival of VIR-O/1645 and *E. coli*-vaccinated mice after lethal challenge (n=5/group). This experiment was repeated two times with identical results. FIG. 3G shows blood cultures from *A. baumannii*-infected patients were plated directly on 0.5× LB agar plates to assess the percentage of VIR-O and AV-T cells present. FIG. 3H shows that for each isolate, AV-T variants were isolated from the VIR-O colonies and the expression of ABUW_1645 was determined in each variant by quantitative real-time PCR. Data represents the mean from three replicates and error bars represent standard deviations of the mean. Student's two-tailed t-test (*p<0.05; p<0.005; *p<0.0005) was used in (B and H). A two-tailed Mann-Whitney test was used in (D) (***p<0.0005). ns, not significant.

FIG. 4A shows the growth curves of VIR-O and AV-T in Chamberlain's minimal media. Values represent (B) Biofilm formation of VIR-O and AV-T cells grown for 24 hours at 25° C. Values represent the average of 6 replicates for each strain. Student's two-tailed t-test was used to determine significance *p<0.0005). FIG. 4C shows the ratio of ABUW_1645 expression in VIR-O and AV-T cells at low (25° C.) and high temperature (37° C.). Values represent the averages of two independent biological replicates. FIG. 4D shows phenotypic switching of VIR-O and AV-T cells at low (25° C.) and high temperature (37° C.) in LB media harvested at an optical density $A_{600}$ of 1.6. Values represent three biological replicates. A two-tailed paired t-test (*p<0.001) was used in (D). All error bars in panels (B-D) represent standard deviations.

FIG. 5A shows a single VIR-O colony after 24 hrs of growth on a 0.5× LB agar plate. At this time, three separate VIR-O colonies were resuspended and dilutions were plated to assess the frequency of cells that switched to AV-T (FIGS. 5B, C). After 24 hours of growth, the switching frequency of three separate AV-T colonies to VIR-O was determined as described above (C). This was then sequentially repeated two additional times.

FIGS. 7A-B show that a highly virulent opaque (VIR-O) population is responsible for systemic infection in mice. Mice were infected intranasally with VIR-O (red) or AV-T (blue) strains. At 24 h.p.i, (A) spleens and (B) livers were harvested and plated for CFU enumeration. Error bars represent geometric mean and Mann-Whitney test (***p<0.0005).

FIG. 8 shows VIR-O cells derived from AV-T colonies regain virulence in mice. Mice were infected intranasally with VIR-O (red) or AV-T (blue) strains. At 24 h.p.i, organs were harvested and plated for CFU enumeration. Error bars represent geometric mean and Mann-Whitney test (***p<0.0005).

FIGS. 9A-C show that the grow rates of VIR-O and AV-T variants were similar in rich media (LB) (FIG. 9A), in a minimal salts media (FIG. 9B) and in a low iron minimal salts media (FIG. 9C).

FIG. 10 shows that VIR-O is resistant to the human antimicrobial peptide LL-37. VIR-O (red) or AV-T (blue) was treated with human antimicrobial peptide LL-37 for 1 hour, and percent survival relative to VIR-O was calculated. Error bars represent standard deviation of the mean and Student's two-tailed t-test (*p<0.05).

FIGS. 14A-D show that VIR-O/1645 is sensitive to desiccation and hospital-used disinfectants. FIGS. 14A and B show VIR-O/vector (red), AV-T/vector (blue), VIR-O/1645 (green) or AV-T/1645 (gold) strains was subjected for desiccation assays. FIG. 14A shows bacteria were rehydrated and plated on day 4 of desiccation to determine viability. FIG. 14B shows recovered bacterial from each cells were assessed for the percentage of VIR-O and AV-T cells present. FIGS. 14C and D show VIR-O/vector (red), AV-T/vector (blue), VIR-O/1645 (green) or AV-T/1645 (gold) strains was treated with the indicated amounts of disinfectants: (A) BZK 0.004% and (B) CHG 0.008%, and CFU was enumerated. Error bars represent standard deviation of the mean and Student's two-tailed t-test (*$p<0.05$; $p<0.005$; *$p<0.0005$). Red and blue asterisks denote significance statistical analysis compared to VIR-O/vector and AV-T/vector, respectively.

FIG. 15A shows qRT-PCR analysis of ABUW_1645 expression in wild-type, a ΔompR mutant and arpB::Tc is shown. The frequency of switching in 24 hr colonies from VIR-O to AV-T is shown in FIG. 15B. Values were determined using clpX as an internal control and ompR value is normalized relative to wild-type.

DETAILED DESCRIPTION

Figures 1A, 1B:
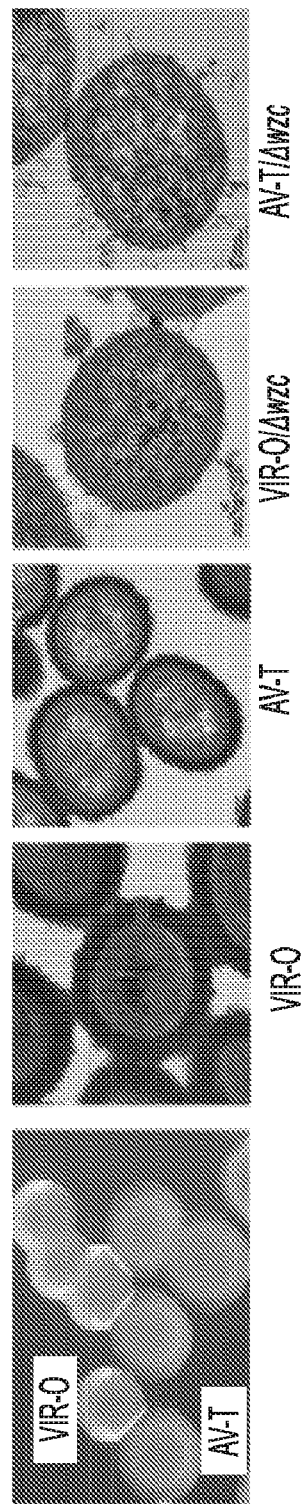

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, the subject is a human. The term does not denote a particular age or sex. Thus, adult, child, adolescent and newborn subjects, as well as fetuses, whether male or female, are intended to be covered.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZΔM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferaseI (galT), feedback-insensitive α subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as 35S or 131I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

As used herein, the term "patient" refers to a subject afflicted with a disease or disorder. The term "patient" includes human and veterinary subjects. In some aspects of the disclosed methods, the "patient" has been diagnosed with a need for treatment for an infection, such as, for example, prior to the administering step.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. For example, the disease, disorder, and/or condition can be an infection or associated with an infection.

As used herein, the terms "inhibit," "inhibiting," and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100 percent, or any amount of reduction in between as compared to native or control levels. In an aspect, the inhibition or reduction is 10-20, 20-30, 30-40, 40-50, 50-60, 60-70, 70-80, 80-90, or 90-100 percent as compared to native or control levels. In an aspect, the inhibition or reduction is 0-25, 25-50, 50-75, or 75-100 percent as compared to native or control levels. Further, the terms, "inhibit" or "inhibiting" mean decreasing microbrial or bacterial colonization from the amount of colonization that would occur without treatment and/or causing an infection to decrease. Inhibiting also include causing a complete regression of the colonization.

As used herein, "modulate" is meant to mean to alter, by increasing or decreasing.

As used herein, "prevent" is meant to mean minimize the chance that a subject who has an increased susceptibility for developing an infection will develop an infection.

As used herein, "treat" is meant to mean administer a compound, composition or molecule of the invention to a subject, such as a human or other mammal (for example, an animal model), that has an infection, in order to prevent or delay a worsening of the effects of the disease or condition, or to partially or fully reverse the effects of the disease.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See *Proteins—Structure and Molecular Properties* 2nd Ed., T. E. Creighton, W.H. Freeman and Company, New York (1993); *Posttranslational Covalent Modification of Proteins*, B. C. Johnson, Ed., Academic Press, New York, pp. 1-12 (1983)).

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, "sample" is meant to mean an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, "effective amount" of a compound is meant to mean a sufficient amount of the compound to provide the desired effect. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

Phenotypic switching is a type of switch that occurs between multiple cellular morphologies. It has been shown that, for example, two different phenotypic subpopulations are present in an isogenic strain culture, known as opaque and translucent, referred to herein as "O" or "VIR-O" and "T" or "AV-T", respectively.

Compositions and Methods

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B—F, C-D, C-E, and C—F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed herein are methods and compositions that can be used to prevent or treat microbial or bacterial infections such as, for example, by a vaccination.

Compositions. In some aspects, the disclosure contemplates inducing and/or maintaining a bacteria or *Acinetobacter* such as *Acinetobacter baumannii* in an avirulet translucent phenotype. In some aspects, the compositions comprise attenuated *Acinetobacter*. In some aspects, the *Acinetobacter* is *Acinetobacter baumannii* and/or *Acinetobacter calcoaceticus*. In some aspects, the compositions comprise attenuated *Acinetobacter*. In some aspects, the *Acinetobacter* is *Acinetobacter baumannii* and/or *Acinetobacter calcoaceticus*. In a further aspect, the attenuated *Acinetobacter* comprises an expression vector comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or variants thereof. In a further aspect, the attenuated *Acinetobacter* comprises an expression vector comprising a nucleic acid encoding the ABUW_1645 protein, PNLEASFRALRVLH-TARDLFKQYGFHKVGVDRIIAESKITKATFYNYFHS-KERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or variants thereof, wherein the ABUW_1645 protein is expressed in a concentration sufficient to induce or maintain the *Acinetobacter baumannii* in a translucent phenotype.

In an aspect, disclosed herein is attenuated *Acinetobacter baumannii*. In an aspect, the attenuated *Acinetobacter baumannii* can comprise an expression vector. In an aspect, the expression vector can comprise a nucleic acid encoding an ABUW_1645 protein or biologically active variant thereof. In an aspect, the ABUW_1645 protein has the sequence set forth in SEQ ID NO: 1. In an aspect, the variant thereof can have a greater than 70%, 80%, 90%, 95%, 96%, 97%, 98%, or 99% identity or similarity to SEQ ID NO: 1. In an aspect, the variant thereof can have the sequence set forth in SEQ ID NO: 2. SEQ ID NO: 2 corresponds to amino acid sequence:
p$X^1$lea$X^2$fralr$X^3$lhtardlf$X^4$qygfhkvgvdriiaeskitkatf ynyfhskerliemcltfqk$X^5$glkeevfsiiysy$X^6$ elmvfdklkk$X^7$fflhanl$X^8$glyrlp$X^9$qaifeiekfypt$X^{10}$ykvvvdyrn wlv$X^{11}$qihqllltika$X^{12}$a$X^{13}$led$X^{14}$ymflfvidgamvqllskdriderd klldyfl$X^{15}X^{16}X^{17}$s. In an aspect, $X^1$ to $X^{17}$ can each be individually and independently any amino acid or a conserved amino acid compared to the corresponding amino acid in SEQ ID NO: 1. In an aspect, the variant thereof can comprise Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1.

In some aspects, the ABUW_1645 variants can have less than 70% identity or similarity to SEQ ID NO: 1. In some aspects, variants thereof can have about 10%, 20%, 30%, 40%, 50%, 60% or 70% identity or similarity to SEQ ID NO: 1. In some aspects, the ABUW_1645 variants can have less than 70% identity or similarity to SEQ ID NO: 1, but can comprise a sequence that is 70%, 80%, 90%, 95%, 96%, 97%, 98%, 99, or 100% identical or similar to the helix-turn-helix region of ABUW_1645 which can be useful for DNA binding. Amino acids 25-60 (FHKVGVDRII-AESKITKATFYNYFHS KERLIEMCLT; SEQ ID NO: 13) of the ABUW_1645 (SEQ ID NO: 1) are highly conserved. This highly conserved region is in the DNA binding domain and can be referred to as the DNA binding domain. Examples of ABUW_1645 homologs include but are not limited to ABUW_1959; ABUW_1163; ABUW_0222; ABUW_2818; and ABUW_2596. In an aspect, proteins that are about 70%, 80%, 90%, 95%, 96%, 97%, 98%, 99, or 100% identity or similarity to the helix-turn-helix region of SEQ ID NO: 1 can bind to the same regions of DNA as ABUW_1645 (SEQ ID NO: 1) and can regulate genes in a similar manner. In some aspects, proteins that are about 70%, 80%, 90%, 95%, 96%, 97%, 98%, 99, or 100% identity or similarity to the helix-turn-helix region of SEQ ID NO: 1 can also switch cells from VIR-O to AV-T. In some aspects, a protein or a ABUW_1645 variant as described herein comprises about 70%, 80%, 90%, 95%, 96%, 97%, 98%, 99, or 100% identity or similarity to SEQ ID NO: 13.

In some aspects, variants thereof can have about 10%, 20%, 30%, 40%, 50%, 60% or 70% identity or similarity to SEQ ID NO: 1 and have 70%, 80%, 90%, 95%, 96%, 97%, 98%, 99, or 100% identity or similarity to SEQ ID NO: 13. In some aspects, variants thereof can have 70%, 80%, 90%, 95%, 96%, 97%, 98%, 99, or 100% identity or similarity to SEQ ID NO: 1 and have 70%, 80%, 90%, 95%, 96%, 97%, 98%, 99, or 100% identity or similarity to SEQ ID NO: 13.

In an aspect, disclosed herein is attenuated *Acinetobacter baumannii* comprising an expression vector comprising a nucleic acid encoding an ABUW_1645 variant. In an aspect, the ABUW_1645 variant can be greater than 70%, 80%, 90%, 95%, 96%, 97%, 98% or 99% identity or similarity to SEQ ID NO: 1. In an aspect, the ABUW_1645 variant can be less than 70%, 80%, 90%, 95%, 96%, 97%, 98% or 99% identity or similarity to SEQ ID NO: 1. In an aspect, the ABUW_1645 variant comprises SEQ ID NO: 13. In an aspect, the ABUW_1645 variant comprises a sequence that can be 70%, 80%, or 90% identical to SEQ ID NO: 13. In an aspect, the ABUW_1645 variant comprises a sequence that can less than 70% identity or similarity to SEQ ID NO: 1 and can have a sequence that can be greater than 70% identity or similar to SEQ ID NO: 13. In an aspect, the ABUW_1645 variant comprises a sequence that can be greater than 70% identity or similarity to SEQ ID NO: 1 and can have a sequence that can be greater than 70% identity or similarity to SEQ ID NO: 13. Also, disclosed herein is an attenuated *Acinetobacter baumannii* comprising an expression vector comprising a nucleic acid that can encode an ABUW_1645 variant, wherein the variant can have a less than 70% identity or similarity to SEQ ID NO: 1 and can have a greater than 70% identity or similarity to SEQ ID NO: 13. Also disclosed herein is an attenuated *Acinetobacter baumannii* comprising an expression vector comprising a nucleic acid that can encode an ABUW_1645 variant, wherein the variant can have a greater than 70% identity or similarity to SEQ ID NO: 1 and can have a greater than 70% identity or similarity to SEQ ID NO: 13.

The term "variant" is contemplated to include functional variants, allelic variants, or active fragments. Variants may include 1 or 2 amino acid substitutions or conserved substitutions. Variants may include 3 or 4 amino acid substitutions or conserved substitutions. Variants may include 5 or 6 or more amino acid substitutions or conserved substitutions. Variant include those with not more than 1% or 2% of the amino acids are substituted. Variant include those with not more than 3% or 4% of the amino acids are substituted. Variants can include proteins with greater than 10%, 20%, 30%, 40%, 50%, 60%, 70%, 80%, 89%, 90%, 95%, 98%, or 99% identity or similarity.

Variants can be tested by mutating a vector to produce appropriate codon alternatives for polypeptide translation. Active variants and fragments can be identified with a high probability using computer modeling. Shihab et al. report an online genome tolerance browser. BMC Bioinformatics. 2017, 18(1):20. Ng et al. report methods of predicting the effects of amino acid substitutions on protein function. Annu Rev Genomics Hum Genet. 2006, 7:61-80. Teng et al. Approaches and resources for prediction of the effects of non-synonymous single nucleotide polymorphism on protein function and interactions. Curr Pharm Biotechnol. 2008, 9(2):123-33.

Guidance in determining which and how many amino acid residues may be substituted, inserted or deleted without abolishing biological activity may be found using computer programs well known in the art, for example, RaptorX, ESyPred3D, HHpred, Homology Modeling Professional for HyperChem, DNAStar, SPARKS-X, EVfold, Phyre, and Phyre2 software. See also Saldano et al. Evolutionary Conserved Positions Define Protein Conformational Diversity, PLoS Comput Biol. 2016, 12(3):e1004775; Marks et al. Protein structure from sequence variation, Nat Biotechnol. 2012, 30(11): 1072-80; Mackenzie et al. Curr Opin Struct Biol. 2017, 44:161-167 Mackenzie et al. Proc Natl Acad Sci USA. 113(47):E7438-E7447 (2016); Joseph et al. J R Soc Interface. 2014, 11(95):20131147, Wei et al. Int. J. Mol. Sci. 2016, 17(12), 2118. Variants can be tested in functional assays. Certain variants have less than 10%, and preferably less than 5%, and still more preferably less than 2% changes (whether substitutions, deletions, and so on).

In some aspects, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In some aspects, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example the polypeptides GGGGGG (SEQ ID NO: 9) and GGGGT (SEQ ID NO: 10) have a sequence identity of 4 out of 5 or 80%. For example, the polypeptides GGGPPP (SEQ ID NO: 11) and GGGAPPP (SEQ ID NO: 12) have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic-A V I L; Charged positive: R K H; Charged negative—D E; Polar—S T N Q. The amino acid groups are also considered conserved substitutions.

In some aspects, the disclosure relates to recombinant polypeptides comprising sequences disclosed herein or variants or fusions thereof wherein the amino terminal end or the carbon terminal end of the amino acid sequence are optionally attached to a heterologous amino acid sequence, label, or reporter molecule.

Vectors.

In certain embodiments, the disclosure relates to the recombinant vectors comprising a nucleic acid encoding a polypeptide disclosed herein or chimeric protein thereof.

Disclosed herein are expression vectors comprising a nucleic acid encoding the ABUW_1645 protein or a variant thereof.

Disclosed herein are expression vectors comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof. Disclosed herein are expression vectors comprising a nucleic acid encoding the ABUW_1645 protein, PNLEASFRALRVLHTARDLFKQYGFHKVGVDRIIAE SKITKATFYNYFHSKERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof wherein the variant has 70%, 80%, 90%, 95%, 96%, 97%, 98%, or 99% identity or similarity to SEQ ID NO: 1. In an aspect, the variant can have the sequence set forth in SEQ ID NO: 2. SEQ ID NO: 2 corresponds to amino acid sequence: p$X^{1}$lea$X^{2}$fralr$X^{3}$lhtardlf$X^{4}$qygfhkvgvdriiaeskitkatfynyfhsk erliemcltfqk$X^{5}$glkeevfsiiysy$X^{6}$ elmvfdklkk$X^{7}$fflhanl$X^{8}$ glyrlp$X^{9}$qaifeiekfypt$X^{10}$ykvvvdyrnwlv$X^{11}$qihqllltika$X^{12}$ a$X^{13}$led$X^{14}$ymflfvidgamvqllskdriderdklldyfl$X^{15}X^{16}X^{17}$s. In an aspect, $X^{1}$ to $X^{17}$ of SEQ ID NO. 2 can each be individually and independently any amino acid or a conserved amino acid compared to the corresponding amino acid in SEQ ID NO: 1. In an aspect, the variant can comprise Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1.

In some aspects, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In some aspects, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

Vaccines.

When a human or non-human animal is challenged by a foreign organism/pathogen the challenged individual responds by launching an immune response which may be protective. This immune response is characterized by the coordinated interaction of the innate and acquired immune response systems.

The innate immune response forms the first line of defense against a foreign organism/pathogen. An innate immune response can be triggered within minutes of infection in an antigen-independent, but pathogen-dependent, manner. The innate, and indeed the adaptive, immune system can be triggered by the recognition of pathogen associated molecular patterns unique to microorganisms by pattern recognition receptors present on most host cells. Once triggered the innate system generates an inflammatory response that activates the cellular and humoral adaptive immune response systems.

The adaptive immune response becomes effective over days or weeks and provides the antigen specific responses needed to control and usually eliminate the foreign organism/pathogen. The adaptive response is mediated by T cells (cell mediated immunity) and B cells (antibody mediated or humoral immunity) that have developed specificity for the pathogen. Once activated these cells have a long lasting memory for the same pathogen.

The ability of an individual to generate immunity to foreign organisms/pathogens, thereby preventing or at least reducing the chance of infection by the foreign organism/pathogen, is a powerful tool in disease control and is the principle behind vaccination.

Vaccines function by preparing the immune system to mount a response to a pathogen. Typically, a vaccine comprises an antigen, which is a foreign organism/pathogen or a toxin produced by an organism/pathogen, or a portion thereof, that is introduced into the body of a subject to be vaccinated in a non-toxic, non-infectious and/or non-pathogenic form. The antigen in the vaccine causes the subject's immune system to be "primed" or "sensitized" to the organism/pathogen from which the antigen is derived. Subsequent exposure of the immune system of the subject to the organism/pathogen or toxin results in a rapid and robust specific immune response, that controls or destroys the organism/pathogen or toxin before it can multiply and infect or damage enough cells in the host organism to cause disease symptoms.

In many cases it is necessary to enhance the immune response to the antigens present in a vaccine in order to stimulate the immune system to a sufficient extent to make a vaccine effective, that is, to confer immunity. To this end, additives known as adjuvants (or immune potentiators) have been devised which enhance the in vivo immune response to an antigen in a vaccine composition.

An adjuvant component can increase the strength and/or duration of an immune response to an antigen relative to that elicited by the antigen alone. A desired functional characteristic of an adjuvant component is its ability to enhance an appropriate immune response to a target antigen.

Disclosed herein are vaccines. In some aspects, the vaccine comprises a heat-killed form of an *Acinetobacter baumannii* or attenuated *Acinetobacter baumannii* (or if any form of a vaccine were to be derived from whole *Acinetobacter* cells). In some aspects the *Acinetobacter baumannii* can be attenuated or inactivated, formulated and administered, according to known methods, as a vaccine to induce an immune response in a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate microbes expressing antigenic determinants of the donor microbe; chemical selection; protein activity and inhibition; and DNA screening (such as probe hybridization or PCR) to confirm that donor genes encoding the antigenic determinants are not present in the attenuated microbes.

In some aspects, the disclosure contemplates inducing and/or maintaining *Acinetobacter* such as *Acinetobacter baumannii* in a translucent phenotype as a vaccine delivery vehicle for other antigens from other pathogens or cancer antigens.

Disclosed herein are vaccine compositions comprising: an attenuated *Acinetobacter baumannii* that exhibits expression of ABUW_1645 protein corresponding to SEQ ID NO: 1 or a variant thereof; and a pharmaceutically acceptable carrier. In an aspect, the variant thereof can have a greater than 70%, 80%, 90%, 95%, 96%, 97%, 98%, or 99% identity or similarity to SEQ ID NO: 1. In an aspect, the variant thereof can have the sequence set forth in SEQ ID NO: 2. SEQ ID NO: 2 corresponds to amino acid sequence: pX$^1$leaX$^2$fralrX$^3$lhtardlfX$^4$qygfhkvgvdriiaeskitkatfynyfhsk erliemcltfqkX$^5$glkeevfsiiysyX$^6$elmvfdklkkX$^7$fflhanlX$^8$ glyrlpX$^9$qaifeiekfyptX$^{10}$ykvvvdyrnwlvX$^{11}$qihqllltikaX$^{12}$ aX$^{13}$ledX$^{14}$ymflfvidgamvqllskdriderdklldyflX$^{15}$X$^{16}$X$^{17}$s. In an aspect, X$^1$ to X$^{17}$ can each be individually and independently any amino acid or a conserved amino acid compared to the corresponding amino acid in SEQ ID NO: 1. In an aspect, the variant thereof can comprise Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1. In some aspects, the ABUW_1645 variants can have less than 70% identity or similarity to SEQ ID NO: 1. In some aspects, variants thereof can have about 10%, 20%, 30%, 40%, 50%, 60% or 70% identity or similarity to SEQ ID NO: 1. In some aspects, the ABUW_1645 variants can have less than 70% identity or similarity to SEQ ID NO: 1, but can comprise a sequence that can be 70%, 80%, 90%, 95%, 96%, 97%, 98%, 99, or 100% identical or similar to the helix-turn-helix region of ABUW_1645 which can be useful for DNA binding. Amino acids 25-60 (FHKVGVDRIIAESKITKATFYNYFHS KERLIEMCLT; SEQ ID NO: 13) of the ABUW_1645 (SEQ ID NO: 1) are highly conserved. These highly conserved regions are in the DNA binding domain or can be referred to as the DNA binding domain. Examples of ABUW_1645 homologs include but are not limited to ABUW_1959; ABUW_1163; ABUW_0222; ABUW_2818; and ABUW_2596. In an aspect, proteins that are about 70%, 80%, 90%, 95%, 96%, 97%, 98%, 99, or 100% identity or similarity to the helix-turn-helix region of SEQ ID NO: 1 can bind to the same regions of DNA as ABUW_1645 (SEQ ID NO: 1) and can regulate genes in a similar manner. In some aspects, proteins that are about 70%, 80%, 90%, 95%, 96%, 97%, 98%, 99, or 100% identity or similarity to the helix-turn-helix region of SEQ ID NO: 1 can also switch cells from VIR-O to AV-T. In some aspects, a protein or a ABUW_1645 variant as described herein comprises about 70%, 80%, 90%, 95%, 96%, 97%, 98%, 99, or 100% identity or similarity to SEQ ID NO: 13. In some aspects, variants thereof can have about 10%, 20%, 30%, 40%, 50%, 60% or 70% identity or similarity to SEQ ID NO: 1 and have 70%, 80%, 90%, 95%, 96%, 97%, 98%, 99, or 100% identity or similarity to SEQ ID NO: 13. In some aspects, variants thereof can have 70%, 80%, 90%, 95%, 96%, 97%, 98%, 99, or 100% identity or similarity to SEQ ID NO: 1 and have 70%, 80%, 90%, 95%, 96%, 97%, 98%, 99, or 100% identity or similarity to SEQ ID NO: 13.

The compositions, immunogenic compositions and vaccines described herein can further comprise one or more adjuvants. The adjuvant can be any composition, pharmacological or immunological agent that modifies the effect of other agents, such as the antigens described herein. Examples of adjuvants include, but are not limited to *Acinetobacter* (e.g. *Acinetobacter baumannii*) lysate (including an *Acinetobacter* whole cell lysate) and an attenuated *Acinetobacter* (including *Acinetobacter baumannii* whole cell lysate), Other examples of adjuvants include evolutionarily conserved molecules, so called PAMPs, which include liposomes, lipopolysaccharide (LPS), molecular cages for antigen, components of bacterial cell walls, and endocytosed nucleic acids such as double-stranded RNA (dsRNA), single-stranded DNA (ssDNA), and unmethylated CpG dinucleotide-containing DNA. Additional examples of adjuvants, include, but are not limited to are aluminum containing adjuvants that include a suspensions of minerals (or mineral salts, such as aluminum hydroxide, aluminum phosphate, aluminum hydroxyphosphate) onto which antigen is adsorbed. Additional examples of adjuvants, include, but are not limited to aluminum-(alum-)free adjuvants, which are formulated in the absence of any such aluminum salts. Alum-free adjuvants include oil and water emulsions, such as water-in-oil, and oil-in-water (and variants thereof, including double emulsions and reversible emulsions), lipo-saccharides, lipopolysaccharides, immunostimulatory nucleic acids (such as CpG oligonucleotides), liposomes, Toll-like receptor agonists (particularly, TLR2, TLR4, TLR7/8 and TLR9 agonists), and various combinations of such components.

In some aspects, compositions, immunogenic compositions and vaccines described herein can further comprise both *Acinetobacter baumannii* whole cell lysate, and an attenuated *Acinetobacter baumannii* whole cell lysate.

The compositions, immunogenic compositions and vaccines described herein can comprise one or more nanoparticles. Examples of nanoparticles (used interchangably with the term "nanocarrier") can be found, for example, in US Patent Application 20100233251. Examples of nanocarriers include, but are not limited to nanocarriers composed of one or more polymers. In some aspects, the one or more polymers can be a water soluble, non-adhesive polymer. In some aspects, polymer can be polyethylene glycol (PEG) or polyethylene oxide (PEO). In some aspects, the polymer can be polyalkylene glycol or polyalkylene oxide. In some aspects, the one or more polymers can be a biodegradable polymer. In some aspects, the one or more polymers can be a biocompatible polymer that can be a conjugate of a water soluble, non-adhesive polymer and a biodegradable polymer. In some embodiments, the biodegradable polymer can be polylactic acid (PLA), poly(glycolic acid) (PGA), or poly(lactic acid/glycolic acid) (PLGA). In some aspects, the nanocarrier can be composed of PEG-PLGA polymers.

In some aspects, the nanocarrier can be formed by self-assembly. Self-assembly refers to the process of the formation of a nanocarrier using components that will orient themselves in a predictable manner forming nanocarriers predictably and reproducably. In some aspects, the nanocarriers can be formed using amphiphillic biomaterials which orient themselves with respect to one another to form nanocarriers of predictable dimension, constituents, and placement of constituents. In some aspects, the nanocarrier can be a microparticle, nanoparticle, or picoparticle. In some aspects, the microparticle, nanoparticle, or picoparticle can be self-assembled.

In some aspects, the nanocarrier has a positive zeta potential. In some aspects, the nanocarrier has a net positive charge at neutral pH. In some aspects, the nanocarrier comprises one or more amine moieties at its surface. In some aspects, the amine moiety can be a primary, secondary, tertiary, or quaternary amine. In some aspects, the amine moiety can be an aliphatic amine. In some aspects, the nanocarrier comprises an amine-containing polymer. In some aspects, the nanocarrier comprises an amine-containing lipid. In some aspects, the nanocarrier comprises a protein or a peptide that can be positively charged at neutral pH. In some aspects, the nanocarrier can be a latex particle. In some aspects, the nanocarrier with the one or more amine moieties on its surface has a net positive charge at neutral pH.

Nanoparticles can aid the delivery of the attenuated *Acinetobacter baumannii* and/or can also be immunogenic. Delivery can be to a particular site of interest, e.g., the mucosa. In some aspects, the nanoparticle can create a timed release of the attenuated *Acinetobacter baumannii* to enhance and/or extend the immune response. In some aspects, the nanoparticle can be associated with the attenuated *Acinetobacter baumannii* such that the composition can elicit an immune response. The association can be, for example, wherein the nanoparticle is coupled or conjugated with the attenuated *Acinetobacter baumannii*. By coupled and conjugated is meant that there is a chemical linkage between the nanoparticle and the attenuated *Acinetobacter baumannii*. In some embodiments, the attenuated *Acinetobacter baumannii* is entrapped or encapsulated within the nanoparticle. In some aspects, the inactivated PRRSV can be entrapped within the nanoparticle by a water/oil/water emulsion method. In some aspects, the nanoparticle can be poly(lactide co-glycolide) (PLGA). Depending on the ratio of lactide to glycolide used for the polymerization, different forms of PLGA can be obtained and utilized. These forms are typically identified in regard to the monomers' ratio used (e.g., PLGA 75:25 identifies a copolymer whose composition is 75% lactic acid and 25% glycolic acid). Different ratios can be used in this invention, e.g., 90:10, 80:20, 70:30, 60:40, 50:50, 40:60, 30:70, 20:80, 10:90, and numbers above and in between these ratios. Additional examples of suitable nanoparticles include but are not limited to chitosin, calcium phosphate, lipids of various bacteria like *E. coli*, mycobactera, leptospira and mixtures thereof. The entrapment (encapsulation) efficiency of attenuated *Acinetobacter baumannii* can vary. In an aspect, the nanoparticle can be 50-55% entrapped/encapsulated, calculated based on amount of total attenuated *Acinetobacter baumannii* protein used in the entrapment. Entrapped attenuated *Acinetobacter baumannii* can be administered as mixtures of entrapped/ encapsulated and unentrapped/unencapsulated antigens or the entrapped/encapsulated antigens can be further purified.

In some aspects, the antigen can be derived from inactivated or killed *Acinetobacter baumannii*. In an aspect, the *Acinetobacter baumannii* is inactivated or killed by UV light. Other means of inactivation include chemical, heat, or radioactivity.

Any suitably immunogenic attenuated *Acinetobacter baumannii* or *Acinetobacter* antigen can be utilized in the composition. The attenuated *Acinetobacter baumannii* antigen can be recombinantly derived.

The disclosed compositions can comprise an attenuated *Acinetobacter baumannii* that is immunogenic. The disclosed compositions can also comprise an attenuated *Acinetobacter baumannii* that comprises *Acinetobacter baumannii* antigens.

Disclosed are compositions comprising virus-like particles (VLPs) and a nanoparticle. The disclosed compositions can comprise a VLP that is immunogenic. VLPs resemble viruses, but are non-infectious because they do not contain any viral genetic material. The expression of viral structural proteins, such as Capsid, can result in the self-assembly of VLPs. VLPs can be produced in a variety of cell culture systems including mammalian cell lines, insect cell lines, yeast, and plant cells. For example, the VLP can be produced by a baculovirus or a plant system. The VLP can be immunogenic.

Described herein are vaccines comprising a composition of this invention in a carrier wherein the vaccine is protective against *Acinetobacter baumannii* infection. The term "immunogenic carrier" as used herein can refer to a first polypeptide or fragment, variant, or derivative thereof which enhances the immunogenicity of a second polypeptide or fragment, variant, or derivative thereof. An "immunogenic carrier" can be fused, to or conjugated/coupled to the desired polypeptide or fragment thereof. See, e.g., European Patent No. EP 0385610 B1, which is incorporated herein by reference in its entirety for its teaching of fusing, conjugating or coupling a polypeptide to a carrier. An example of an "immunogenic carrier" is PLGA. In some aspects, the vaccine can comprise whole virus attenuated *Acinetobacter baumannii*, encapsulated by PLGA, and a carrier. In some aspects, the vaccine can further comprise an attenuated *Acinetobacter baumannii* whole cell lysate.

In some aspects, the attenuated *Acinetobacter baumannii* can comprise an expression vector comprising a nucleic acid encoding an ABUW_1645 protein or variant thereof. In an aspect, the ABUW_1645 protein can be SEQ ID NO: 1. In an aspect, the variant thereof can have greater than 70%, 80%, 90%, 95%, 96%, 97%, 98% or 99% identity or similarity to SEQ ID NO: 1. In an aspect, the variant thereof can be the amino acid sequence set forth in SEQ ID NO: 2. In an aspect, the amino acid sequence set forth in SEQ ID NO: 2, $X^1$ to $X^{17}$ can each be individually and independently any amino acid or a conserved amino acid compared to the corresponding amino acid in SEQ ID NO: 1. In an aspect, the variant thereof can comprise Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1. In some aspects, the ABUW_1645 variants can have less than 70% identity or similarity to SEQ ID NO: 1. In some aspects, variants thereof can have about 10%, 20%, 30%, 40%, 50%, 60% or 70% identity or similarity to SEQ ID NO: 1. In some aspects, the ABUW_1645 variants can have less than 70% identity or similarity to SEQ ID NO: 1, but can comprise a sequence that can be 70%, 80%, 90%, 95%, 96%, 97%, 98%, 99, or 100% identical or similar to the helix-turn-helix region of ABUW_1645 which can be useful for DNA binding. Amino acids 25-60 (FHKVGVDRII-AESKITKATFYNYFHS KERLIEMCLT; SEQ ID NO: 13) of the ABUW_1645 (SEQ ID NO: 1) are highly conserved. These highly conserved regions are in the DNA binding domain or can be referred to as the DNA binding domain. Examples of ABUW_1645 homologs include but are not limited to ABUW_1959; ABUW_1163; ABUW_0222; ABUW_2818; and ABUW_2596. In an aspect, proteins that are about 70%, 80%, 90%, 95%, 96%, 97%, 98%, 99, or 100% identity or similarity to the helix-turn-helix region of SEQ ID NO: 1 can bind to the same regions of DNA as ABUW_1645 (SEQ ID NO: 1) and can regulate genes in a similar manner. In some aspects, proteins that are about 70%, 80%, 90%, 95%, 96%, 97%, 98%, 99, or 100% identity or similarity to the helix-turn-helix region of SEQ ID NO: 1 can also switch cells from VIR-O to AV-T. In some aspects, a protein or a ABUW_1645 variant as described herein comprises about 70%, 80%, 90%, 95%, 96%, 97%, 98%, 99, or 100% identity or similarity to SEQ ID NO: 13. In some aspects, variants thereof can have about 10%, 20%, 30%, 40%, 50%, 60% or 70% identity or similarity to SEQ ID NO: 1 and have 70%, 80%, 90%, 95%, 96%, 97%, 98%, 99, or 100% identity or similarity to SEQ ID NO: 13. In some aspects, variants thereof can have 70%, 80%, 90%, 95%, 96%, 97%, 98%, 99, or 100% identity or similarity to SEQ ID NO: 1 and have 70%, 80%, 90%, 95%, 96%, 97%, 98%, 99, or 100% identity or similarity to SEQ ID NO: 13.

In still a further aspect, the *Acinetobacter* comprises attenuated *Acinetobacter* comprising an expression vector comprising a nucleic acid encoding the ABUW_1645 protein and optionally a full or partial deletion in the TrxA coding region or gene, resulting in a non-functional TrxA gene. See WO2017004545. In other aspects, the TrxA gene can be mutated to abolish or reduce the function of the TrxA protein, with the reduction of function being to a level that results in the attenuation of the bacteria.

Methods.

Disclosed herein are methods of vaccinating against *Acinetobacter baumannii*. Described herein are methods of eliciting an immune response against *Acinetobacter* comprising administering to a subject a composition of the invention. The immune response can be protective. The method can further comprise administering to the subject attenuated *Acinetobacter* to monitor the vaccine efficacy. Described herein are methods of eliciting an immune response against *Acinetobacter* comprising administering to a subject a composition an attenuated *Acinetobacter baumannii*.

In an aspect, the method can comprise administering an *Acinetobacter baumannii* or attenuated *Acinetobacter baumannii* as disclosed herein to a subject in need thereof. Also disclosed herein are methods of treating an *Acinetobacter baumannii* infection. In an aspect, the method can comprise administering an *Acinetobacter baumannii* or attenuated *Acinetobacter baumannii* as disclosed herein to a subject in need thereof. The expression "immunologically-effective amount" means that amount of vaccine composition required to invoke the production of protective levels of antibodies in a mammal upon vaccination. The vaccine composition can be administered to the mammal in any manner known in the art including oral, intranasal, mucosal, topical, transdermal, and parenteral (e.g., intravenous, intraperitoneal, intradermal, subcutaneous or intramuscular) routes. Administration can also be achieved using needle-free delivery devices. Administration can be achieved using a combination of routes, e.g., first administration using a parental route and subsequent administration using a mucosal route, etc.

Disclosed herein, are methods of treating a subject with an infection. In an aspect, the method comprises: (a) identifying a subject in need of treatment; and (b) administering to the subject a therapeutically effective amount of the pharmaceutical composition comprising attenuated *Acinetobacter baumannii* and a pharmaceutically acceptable carrier. The attenuated *Acinetobacter baumannii* can be any of the nucleic acid sequences encoding an ABUW_1645 protein or variants thereof disclosed herein.

Disclosed herein, are methods of preventing an infection caused by *Acinetobacter baumannii* in a subject. The method can comprise: (a) identifying a subject in need of treatment; and (b) administering to the subject a therapeutically effective amount of the pharmaceutical composition comprising attenuated *Acinetobacter baumannii* and a pharmaceutically acceptable carrier. The attenuated *Acinetobacter baumannii* can be any of the nucleic acid sequences encoding an ABUW_1645 protein or variants thereof disclosed herein.

Disclosed herein, are methods of reducing risk of an infection caused by *Acinetobacter baumannii* in a subject. The method can comprise: (a) identifying a subject in need of treatment; and (b) administering to the subject a therapeutically effective amount of the pharmaceutical composition comprising attenuated *Acinetobacter baumannii* and a pharmaceutically acceptable carrier. The attenuated *Acinetobacter baumannii* can be any of the nucleic acid sequences encoding an ABUW_1645 protein or variants thereof disclosed herein.

Disclosed herein, are methods of preventing colonization of *Acinetobacter baumannii* in a subject. The method can comprise: (a) identifying a subject in need of treatment; and (b) administering to the subject a therapeutically effective amount of the pharmaceutical composition comprising attenuated *Acinetobacter baumannii* and a pharmaceutically acceptable carrier. The attenuated *Acinetobacter baumannii* can be any of the nucleic acid sequences encoding an ABUW_1645 protein or variants thereof disclosed herein.

Disclosed herein, are methods of immunizing a subject. The method can comprise administering one or more of the vaccines described herein. In an aspect, the vaccine can be a composition comprising an attenuated *Acinetobacter baumannii* expressing ABUW_1645 protein corresponding to SEQ ID NO: 1 or a variant thereof; and a pharmaceutically acceptable carrier. In an aspect, the vaccine composition can be administered to the subject by direct injection or spray administration. In an aspect, the method can further include the step of identifying a subject in need thereof.

Disclosed herein, are methods of providing immunological protection to a subject from an infection caused by *Acinetobacter baumannii* in the subject. The method can comprise (a) identifying a subject in thereof; and (b) administering to the subject an effective amount of an attenuated *Acinetobacter baumannii*, wherein the attenuated *Acinetobacter baumannii* comprises ABUW_1645 protein corresponding to SEQ ID NO: 1 or a variant thereof.

Certain aspects of this disclosure are directed to methods of administering antibacterial compositions to patients before exposure or shortly after exposure to bacterial agents. The term "shortly after" refers to administering treatment within 1, 6, 12, 24, 36, 48, 60, or 72 hours, or 1, 2, 3, 4, 5, 6, or 7 days or any time in between after suffering trauma (e.g., open wound) or presentation of gastrointestinal symptoms. Such treatment can depress the viability or virulence of bacterial agents and prevent, mitigate, or hinder infection, or the development of disease caused by these bacterial agents. In certain aspects, the bacterial agent is an *Acinetobacter*. In a further aspect, the bacterial agent is a live attenuated *Acinetobacter baumannii*. As used herein, the term "live attenuated vaccine" or "live attenuated bacteria" is known in the art and refers to a vaccine containing live micro-organisms that have attenuated or decreased virulent properties or which contains closely-related but less virulent organisms to evoke a broad immune response. In an aspect, the attenuated *Acinetobacter baumannii* can be live attenuated *Acinetobacter baumannii*.

Certain embodiments are directed to methods of treating or preventing *Acinetobacter baumannii* colonization or infection or disease caused by an *Acinetobacter baumannii* microbe. In some aspects, the methods are directed to immunizing a subject. In some aspects, the methods are directed to reducing risk of infection caused by *Acinetobacter baumannii* in as subject. In an aspect, the methods can comprise administering a clinically effective dose of an attenuated bacteria to a subject in need thereof. In some aspects, the attenuated bacteria can be *Acinetobacter baumannii*. In some aspects, the attenuated *Acinetobacter baumannii* can comprise an expression vector. In an aspect, the expression vector can express an ABUW_1645 protein or variant thereof. In an aspect, the ABUW_1645 protein can be SEQ ID NO: 1. In an aspect, the variant thereof can have greater than 70%, 80%, 90%, 95%, 96%, 97%, 98% or 99% identity or similarity to SEQ ID NO: 1. In an aspect, the variant thereof can be the amino acid sequence set forth in SEQ ID NO: 2. In an aspect, the amino acid sequence set forth in SEQ ID NO: 2, $X^1$ to $X^{17}$ can each be individually and independently any amino acid or a conserved amino acid compared to the corresponding amino acid in SEQ ID NO: 1. In an aspect, the variant thereof can comprise Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1. In some aspects, the ABUW_1645 variants can have less than 70% identity or similarity to SEQ ID NO: 1. In some aspects, variants thereof can have about 10%, 20%, 30%, 40%, 50%, 60% or 70% identity or similarity to SEQ ID NO: 1. In some aspects, the ABUW_1645 variants can have less than 70% identity or similarity to SEQ ID NO: 1, but can comprise a sequence that can be 70%, 80%, 90%, 95%, 96%, 97%, 98%, 99, or 100% identical or similar to the helix-turn-helix region of ABUW_1645 which can be useful for DNA binding. Amino acids 25-60 (FHKVGVDRIIAESKITKAT-FYNYFHS KERLIEMCLT; SEQ ID NO: 13) of the ABUW_1645 (SEQ ID NO: 1) are highly conserved. These highly conserved regions are in the DNA binding domain or can be referred to as the DNA binding domain. Examples of ABUW_1645 homologs include but are not limited to ABUW_1959; ABUW_1163; ABUW_0222; ABUW_2818; and ABUW_2596. In an aspect, proteins that are about 70%, 80%, 90%, 95%, 96%, 97%, 98%, 99, or 100% identity or similarity to the helix-turn-helix region of SEQ ID NO: 1 can bind to the same regions of DNA as ABUW_1645 (SEQ ID NO: 1) and can regulate genes in a similar manner. In some aspects, proteins that are about 70%, 80%, 90%, 95%, 96%, 97%, 98%, 99, or 100% identity or similarity to the helix-turn-helix region of SEQ ID NO: 1 can also switch cells from VIR-O to AV-T. In some aspects, a protein or a ABUW_1645 variant as described herein comprises about 70%, 80%, 90%, 95%, 96%, 97%, 98%, 99, or 100% identity or similarity to SEQ ID NO: 13. In some aspects, variants thereof can have about 10%, 20%, 30%, 40%, 50%, 60% or 70% identity or similarity to SEQ ID NO: 1 and have 70%, 80%, 90%, 95%, 96%, 97%, 98%, 99, or 100% identity or similarity to SEQ ID NO: 13. In some aspects, variants thereof can have 70%, 80%, 90%, 95%, 96%, 97%, 98%, 99, or 100% identity or similarity to SEQ ID NO: 1 and have 70%, 80%, 90%, 95%, 96%, 97%, 98%, 99, or 100% identity or similarity to SEQ ID NO: 13.

Disclosed herein are methods of treating or preventing colonization, infection, or disease by a *Acinetobacter baumannii* microbe comprising administering a clinically effective dose of an attenuated *Acinetobacter baumannii* to a subject in need thereof, wherein the attenuated *Acinetobacter baumannii* comprises an expression vector expressing a variant, wherein the variant has a less than 70% identity or similarity to SEQ ID NO: 1 and has a greater than 70% identity or similarity to SEQ ID NO: 13.

Disclosed herein are methods of treating or preventing colonization, infection, or disease by a *Acinetobacter baumannii* microbe comprising administering a clinically effective dose of an attenuated *Acinetobacter baumannii* to a subject in need thereof, wherein the attenuated *Acinetobacter baumannii* comprises an expression vector expressing a variant, wherein the variant has a greater than 70% identity or similarity to SEQ ID NO: 1 and has a greater than 70% identity or similarity to SEQ ID NO: 13.

In any of the methods disclosed herein, an *Acinetobacter baumannii* or attenuated *Acinetobacter baumannii* can be administered in combination with one or more antibiotics or antimicrobial agents. As used herein, the term "combination with" when used to describe administration with an additional treatment means that one or more agents may be administered prior to, together with, or after the additional treatment, or a combination thereof. In an aspect, the antibiotic agent can be imipenem, meropenem, or colistin. In some aspects, the attenuated *Acinetobacter baumannii* can be administered before the administration of an antibiotic or antimicrobial agent. In some aspects, the attenuated *Acinetobacter baumannii* can be administered after the administration of an antibiotic or antimicrobial agent. In some aspects, the attenuated *Acinetobacter baumannii* can be administered simultaneous with the administration of an antibiotic or antimicrobial agent. For example, the antibiotic agent can be a carbapenem or colistin.

Disclosed herein are methods of treating or preventing *Acinetobacter baumannii* colonization or infection. In an aspect, the methods can comprise administering a clinically effective dose of an attenuated *Acinetobacter baumannii* to a subject in need thereof. In certain aspects, the attenuated *Acinetobacter baumannii* can be administered before the administration of an antimicrobial agent. In certain aspects, the attenuated *Acinetobacter baumannii* can be administered orally. In certain aspects, the attenuated *Acinetobacter baumannii* can be administered as a live attenuated *Acinetobacter baumannii*. In some aspects, a composition (e.g., vaccine) can be formulated for effective administration through inclusion of additional agents such as excipients, adjuvants, preservatives, stabilizing agents, salts, buffering agents, immunogenic agents, and the like.

In some aspects, the method for treating or preventing bacterial infection in a subject involves administering a bacterial composition described herein. In some embodiments, the composition used for treating or preventing bacterial infection or providing immunological protection can be formulated for effective administration through inclusion of additional agents (e.g., adjuvants, preservatives, stabilizing agents, salts, buffering agents, immunogenic agents). In certain aspects, the method for treating or preventing bacterial infection or providing immunological protection is not limited to any particular dose or treatment regime. Amounts effective can depend on the severity of the infection or the likelihood or risk of infection and the weight and general state and health of the subject. Suitable regimes for initial administration and booster administrations are typified by an initial administration followed by repeated doses at one or more hourly, daily, weekly, or monthly intervals by a subsequent administration. The composition may be administered at least once; twice; three times; four times; 5-10 times; 10-20 times; 20-100 times; 100 times or more or any number in between. In further aspects, the methods described herein are not limited by the duration of time between repetitive administrations of the composition or by the duration of time between administration of the composition and challenge or exposure to a pathogenic agent. The duration of time may be 0 days; 1 day; 2 days; 3 days; 4 days; 5 days; 5-7 days; 1-2 weeks; 2-4 weeks; 4-8 weeks; 8-10 weeks; 10-31 weeks; 31-52 weeks; 1-5 years; 5-10 years; 10-20 years; 20-50 years; 50-100 years or more or any time in between. In some aspects, the subject can be tested for the presence of an infection prior to administration of the composition. In some aspects, the subject is not tested for the presence of an infection prior to the administration of the composition. In some aspects, the subject can be tested for infection following administration of the composition. Such testing may be conducted less than one day, 1-2 days, 2-4 days, 4-6 days, 6-8 days, 8-10 days, 10-15 days, 15-20 days, 20-30 days, 30 or more days or any number of days in between prior to administration of the composition.

In some aspects, compositions and methods of administering these compositions to patients are intended to be used before exposure or after exposure to *Acinetobacter baumannii*. In some aspects, the patient has an *Acinetobacter baumannii* infection. In still other aspects, the patient can be diagnosed with or has a high probability of being diagnosed with an *Acinetobacter baumannii* infection. In some aspects, the patient can be suspected of being exposed to *Acinetobacter baumannii* in a hospital or other medical facility. In some aspects, the patient can be at risk of infection, i.e., the patient can be physically located, was wounded in, or was present in a location or facility that harbors or has harbored *Acinetobacter baumannii*. In a further aspect, the patient can be on mechanical ventilation, has sustained traumatic injuries, and/or can be burned. In some aspects, the patient can be identified as having a previous or current gastrointestinal colonization by *Acinetobacter*. In some aspects, the patient has been wounded. In a further aspect, a patient or subject can a veterinary patient or subject, e.g., livestock such as goat, cattle, sheep; or domesticated animal such as dogs and cats. In some aspects, the subject or patient can be a human subject or a human patient. In some aspects, the human subject or human patient can be military personnel. In some aspects, the human subject or human patient can be administered a vaccine as disclosed herein prior to deployment for combat.

In some aspects, the patient can diagnosed with or has a high probability of being diagnosed with *Acinetobacter baumannii* wound colonization or infection. In some aspects, the patient can be diagnosed with or has a high probability of being diagnosed with *Acinetobacter baumannii* related pneumonia. In some aspects, the patient can be diagnosed with or has a high probability of being diagnosed with *Acinetobacter baumannii* that can be resistant to antibiotics or other conventional anti-microbial drugs.

Pharmaceutical Compositions

In some aspects, this disclosure contemplates pharmaceutical compositions comprising compositions disclosed herein and a pharmaceutically acceptable excipient. In some aspects, this disclosure contemplates the production of a medicament comprising compositions disclosed herein and uses for methods disclosed herein.

Disclosed herein are pharmaceutical compositions comprising an attenuated *Acinetobacter baumannii* comprising an expression vector comprising a nucleic acid encoding the ABUW_1645 protein, PNLEASFRALRVLH-TARDLFKQYGFHKVGVDRIIAE SKITKATFYNYFHS-KERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant has greater than 70%, 80%, 90%, 95%, 96%, 97%, 98% or 99% identity or similarity to SEQ ID NO:1; and a pharmaceutically acceptable excipient.

Disclosed herein are pharmaceutical compositions comprising an attenuated *Acinetobacter baumannii* comprising an expression vector comprising a nucleic acid encoding the ABUW_1645 protein, PNLEASFRALRVLH-TARDLFKQYGFHKVGVDRIIAE SKITKATFYNYFHS-KERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises a nucleic acid encoding the amino acid sequence pX$^1$leaX$^2$fralrX$^3$lhtardlfX$^4$qygfhkvgvdriiaeskitkatfynyfhskerliemcltfqkX$^5$glkeevfsiiysyX$^6$elmvfdklkkX$^7$fflhanlX$^8$glyrlpX$^9$qaifeiekfyptX$^{10}$ykvvvdyrnwlvX$^{11}$qihqllltikaX$^{12}$aX$^{13}$ledX$^{14}$ymflfvidgamvqllskdriderdklldyflX$^{15}$X$^{16}$X$^{17}$s (SEQ ID NO: 2), wherein X$^1$ to X$^{17}$ are each individually and independently any amino acid or a conserved amino acid compared to the corresponding amino acid in SEQ ID NO: 1; and a pharmaceutically acceptable excipient.

Disclosed herein are pharmaceutical compositions comprising an attenuated *Acinetobacter baumannii* comprising an expression vector comprising a nucleic acid encoding the ABUW_1645 protein, PNLEASFRALRVLH-TARDLFKQYGFHKVGVDRIIAE SKITKATFYNYFHS-KERLIE MCLTFQKDGLKEEVF SIIYSYRELMVFDKLKKIFFLHANLEGLYRLPLQAI-FEIEKF YPTAYKVVVDYRNWLVTQIHQLLL-TIKATATLEDAYMFLFVIDGAMVQLLSKD RIDER-DKLLDYFLIILS (SEQ ID NO: 1), or a variant thereof, wherein the variant comprises Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1; and a pharmaceutically acceptable excipient.

In an aspect, the variant thereof can have a greater than 70%, 80%, 90%, 95%, 96%, 97%, 98%, or 99% identity or similarity to SEQ ID NO: 1. In an aspect, the variant thereof can have the sequence set forth in SEQ ID NO: 2. SEQ ID NO: 2 corresponds to amino acid sequence: pX$^1$leaX$^2$fralrX$^3$lhtardlfX$^4$qygfhkvgvdriiaeskitkatfynyfhskerliemcltfqkX$^5$glkeevfsiiysyX$^6$ elmvfdklkkX$^7$fflhanlX$^8$glyrlpX$^9$qaifeiekfyptX$^{10}$ykvvvdyrnwlvX$^{11}$qihqllltikaX$^{12}$aX$^{13}$ledX$^{14}$ymflfvidgamvqllskdriderdklldyflX$^{15}$X$^{16}$X$^{17}$s. In an aspect, X$^1$ to X$^{17}$ can each be individually and independently any amino acid or a conserved amino acid compared to the corresponding amino acid in SEQ ID NO: 1. In an aspect, the variant thereof can comprise Genebank Sequence ID WP_001133118.1, WP_005138665.1, WP_033107856.1, WP_001133117.1, WP_032059603.1, WP_002046920.1, WP_001133086.1, WP_031993083.1, WP_049068495.1, WP_023896536.1, WP_064479198.1, WP_001133115.1, WP_031998507.1, WP_083028705.1, WP_017816824.1, WP_032000726.1, WP_065718791.1, or WP_001133114.1. In some aspects, the ABUW_1645 variants can have less than 70% identity or similarity to SEQ ID NO: 1. In some aspects, variants thereof can have about 10%, 20%, 30%, 40%, 50%, 60% or 70% identity or similarity to SEQ ID NO: 1. In some aspects, the ABUW_1645 variants can have less than 70% identity or similarity to SEQ ID NO: 1, but can comprise a sequence that can be 70%, 80%, 90%, 95%, 96%, 97%, 98%, 99, or 100% identical or similar to the helix-turn-helix region of ABUW_1645 which can be useful for DNA binding. Amino acids 25-60 (FHKVGVDRIIAESKITKATFYNYFHS KER-LIEMCLT; SEQ ID NO: 13) of the ABUW_1645 (SEQ ID NO: 1) are highly conserved. These highly conserved regions are in the DNA binding domain or can be referred to as the DNA binding domain. Examples of ABUW_1645 homologs include but are not limited to ABUW_1959; ABUW_1163; ABUW_0222; ABUW_2818; and ABUW_2596. In an aspect, proteins that are about 70%, 80%, 90%, 95%, 96%, 97%, 98%, 99, or 100% identity or similarity to the helix-turn-helix region of SEQ ID NO: 1 can bind to the same regions of DNA as ABUW_1645 (SEQ ID NO: 1) and can regulate genes in a similar manner. In some aspects, proteins that are about 70%, 80%, 90%, 95%, 96%, 97%, 98%, 99, or 100% identity or similarity to the helix-turn-helix region of SEQ ID NO: 1 can also switch cells from VIR-O to AV-T. In some aspects, a protein or a ABUW_1645 variant as described herein comprises about 70%, 80%, 90%, 95%, 96%, 97%, 98%, 99, or 100% identity or similarity to SEQ ID NO: 13. In some aspects, variants thereof can have about 10%, 20%, 30%, 40%, 50%, 60% or 70% identity or similarity to SEQ ID NO: 1 and have 70%, 80%, 90%, 95%, 96%, 97%, 98%, 99, or 100% identity or similarity to SEQ ID NO: 13. In some aspects, variants thereof can have 70%, 80%, 90%, 95%, 96%, 97%, 98%, 99, or 100% identity or similarity to SEQ ID NO: 1 and have 70%, 80%, 90%, 95%, 96%, 97%, 98%, 99, or 100% identity or similarity to SEQ ID NO: 13.

Pharmaceutical compositions typically comprise an effective amount of compounds and a suitable pharmaceutical acceptable carrier. The preparations can be prepared in a manner known per se, which usually involves mixing the compounds according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

In some aspects, the disclosure relates to pharmaceutical compositions comprising compounds disclosed herein and a pharmaceutically acceptable excipient. In some aspects, the composition can be a tablet or pill or in a capsule or the composition can be an aqueous buffer, e.g., a pH between 6 and 8. In some aspects, the pharmaceutically acceptable excipient can be selected from a filler, glidant, binder, disintegrant, lubricant, and saccharide. Optionally, the pharmaceutical composition further comprises a second clotting agent such as aminocaproic acid (ε-aminocaproic acid), tranexamic acid, fibrinogen, and vitamin K.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the compounds may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Liquid dosage forms for oral administration include pharmaceutically acceptable emulsions, solutions, suspensions, syrups, and elixirs. In addition to the compounds, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, viscoleo, castor oil and sesame oil, glycerol, tetrahydrofurfuryl alcohol, polyethyleneglycols and fatty acid esters of sorbitan or mixtures of these substances, and the like.

In some aspects, production processes are contemplated which two components, compounds disclosed herein and a pharmaceutical carrier, are provided already in a combined dry form ready to be reconstituted together. In some aspects, it is contemplated that compounds disclosed herein and a pharmaceutical carrier are admixed to provide a pharmaceutical composition.

Providing a pharmaceutic composition is possible in a one-step process, simply by adding a suitable pharmaceutically acceptable diluent to the composition in a container. In some aspects, the container can be preferably a syringe for administering the reconstituted pharmaceutical composition after contact with the diluent. In some aspects, the coated compounds can be filled into a syringe, and the syringe can then be closed with the stopper. A diluent can be used in an amount to achieve the desired end-concentration. The pharmaceutical composition may contain other useful component, such as ions, buffers, excipients, stabilizers, etc.

A "dry" pharmaceutical composition typically has only a residual content of moisture, which may approximately correspond to the moisture content of comparable commercial products, for example, has about 12% moisture as a dry product. Usually, the dry pharmaceutical composition according to the present invention has a residual moisture content preferably below 10% moisture, more preferred below 5% moisture, especially below 1% moisture. The pharmaceutical composition can also have lower moisture content, e.g., 0.1% or even below. In some aspects, the pharmaceutical composition can be provided in dry in order to prevent degradation and enable storage stability.

A container can be any container suitable for housing (and storing) pharmaceutically compositions such as syringes, vials, tubes, etc. The pharmaceutical composition may then preferably be applied via specific needles of the syringe or via suitable catheters. A typical diluent comprises water for injection, and NaCl (preferably 50 to 150 mM, especially 110 mM), $CaCl_2$ (preferably 10 to 80 mM, especially 40 mM), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.2 to 7.5, especially at pH of 6.9 to 7.1.

In some aspects, the diluent can be provided in a separate container. This can preferably be a syringe. The diluent in the syringe can then easily be applied to the container for reconstitution of the dry compositions. If the container is also a syringe, both syringes can be finished together in a pack. It is therefore preferred to provide the dry compositions in a syringe, which is finished with a diluent syringe with a pharmaceutically acceptable diluent for reconstituting, said dry and stable composition.

Kits

In some aspects, this disclosure contemplates a kit comprising a pharmaceutical composition disclosed herein and a container with a suitable diluent. Further components of the kit may be instructions for use, administration means, such as syringes, catheters, brushes, etc. (if the compositions are not already provided in the administration means) or other components necessary for use in medical (surgical) practice, such as substitute needles or catheters, extra vials or further wound cover means. In some aspects, the kit comprises a syringe housing the dry and stable hemostatic composition

EXAMPLES

Example 1: ABUW_1645 is a Global Regulator Controlling Phenotypic Switching and Virulence Phenotypic switching is a type of switch that occurs between multiple cellular morphologies. It has been shown that, for example, two different phenotypic subpopulations are present in an isogenic strain culture, known as opaque and translucent, referred to as "O" or "VIR-O" and "T" or "AV-T", respectively. O and T are genetically identical and interconvert. This phenomenon also occurs Acinetobacter baumannii. Described herein is a high frequency phenotypic switch in multidrug resistant A. baumannii. It is roles of these two phenotypic diverse A. baumannii subpopulations in causing infections, surviving in the harsh environment of a hospital and its clinical relevance in human infections.

To understand the pathogenesis of an antibody that was produced by O and T, a mouse pneumonia model was established. Mice were infected intranasally with O and T. At 24 h post infection, the O-infected mice harbored 4.5 logs more bacteria in the lungs than the T-infected mice. In additional, 3 logs more bacteria were recovered in the spleens and livers from the O-infected mice, demonstrating a systemic virulent infection by the O variants.

As the O and T variants interconvert in vitro, it was tested whether this phenotypic switching also occurs in vivo. For this, mice were infected with almost pure O and T cultures, and the percentages of O and T were quantified for the colonies that recovered from the mice lungs. In the T infection model, mice were infected with a culture that contained about 99.91% of T population. Surprisingly, there was a drastic increase in the O population, about 36% at 24 hours, demonstrating a strong selective pressure for the O population in vivo. On the other hand, the O population was observed in the O-infected lungs. Next, a lethal infection was performed and mice survival was monitored over a period often days. The O-infected mice rapidly succumbed to disease by day 2, but T-infected mice survived during the 10 day course of the experiment. These data show that the highly virulent O subpopulation causes disease during in vivo infection.

The lung environment is replete with host innate immune defense mechanisms to eliminate bacterial infections. Time-kill assays were performed by exposing an equal mixture of O and T to $H_2O_2$, murine cationic antimicrobial peptide (CRAMP) and lysozymes. Percent survival relative to O were determined after 1 hour. The results show that O is resistant to $H_2O_2$, CRAMP and lysozyme as compared to T, demonstrating that the highly virulent O subpopulation is resistant to host antimicrobials. Next, it was examined whether host innate defenses contributed to the selection of the virulent O during in vivo infection. Wild-type (WT) mice and triple knockout (TKO) mice lacking a functional NADPH oxidase $cybb^{-/-}$ (required for the production of reactive oxygen species), lysozyme $lysM^{-/-}$ and CRAMP $cnlp^{-/-}$ were infected with T. At 8 hours post infection, approximately 7% of O were recovered from the WT-infected lungs but about 1.5% of O were found in the TKO. These data demonstrate that lung innate immune defenses are selecting a resistant and virulent O population during in vivo infection.

The ability of A. baumannii to persist in the healthcare setting is problematic and serves as a source of infection in hospitals, particularly within ICU wards. O and T cultures were subjected to a desiccation survival assay to test whether the host antimicrobials-resistant O population could survive better in the environment. Bacteria were rehydrated and plated to determine viability. On day 8, most of the T population were dead. Interestingly, the 60% of the remaining viable T population were switched to O during desiccation, suggesting that the O population survives better than the T population on dry surfaces. Next, the O and T were tested for sensitivity to three of the most commonly used hospital disinfectants, benzethonium chloride (BZT), benzalkonium chloride (BAK) and chlorhexidine gluconate (CHG). The results show that the O population was more resistant to the three tested disinfectants. The results also demonstrate that the resistance of the O subpopulation to desiccation and hospital disinfectants, highlighting the risk of persistent of the virulent form of A. baumannii in the hospital environment. In summary, A. baumannii O subpopulation is virulent in mice and resistant to host antimicrobials, desiccation and disinfectants. T, on the other hand, is avirulent and susceptible to host antimicrobials and cannot survive better in hospital settings.

To test whether opaque variants can be recovered from human A. baumannii bloodstream infections, patients' blood cultures from A. baumannii infections were obtained. The blood cultures were directly plated and colonies were checked. The results show that the O population was exclusively detected in the patients' blood cultures. These data highlight the virulent form of A. baumannii is selected in human patients.

To understand the molecular mechanism for the differential phenotypes between the O and T populations, RNA-Seq was performed to examine whether there were transcriptional differences between the virulent O and avirulent T populations. Among the up-regulated genes, a predicted TetR-type transcriptional regulator, ABUW_1645 was highly regulated in the T. The RNASeq data by validated by using quantitative real-time PCR. ABUW-1645 expression was highly overexpressed in T compared to O. These experiments were followed by determining the correlation between O and T phenotypic switch and 1645 expression. 1645 expression was quantified from O and T cultures over a 24-hour time course. 1645 expression was reduced significantly when T cells gradually switched to O, whereas its expression level in the O cultures remained low throughout the 24-hour time course. To further characterize this, 1645 was overexpressed in O and T backgrounds. Strikingly, the O population overexpressed 1645 now showed the T opacity phenotype and were unable to switch back to the O. The T population that overexpressed 1645 also retained the T phenotype and was also unable to switch back to the O form. These data show that constitutive expression of 1645 is required to convert the O phenotype to T and lock them in this state. Furthermore, overexpression of 1645 in the O population conferred increased susceptibility to lysozyme, $H_2O_2$ and CRAMP.

Since the opaque cells that overexpressed 1645 exhibited increased susceptibility to host antimicrobials in vitro and was morphologically similar and locked to the T state, the O/1645 strain was tested to see if it was similarly attenuated for virulence in mice. At 24 hours post infection, both the O and T strains that overexpressed 1645 were highly attenuated in mice, exhibiting about 7 logs lower bacterial loads in the lungs compared to O, and about 2 logs lower loads compared to T. It was hypothesized that the frequency of the phenotypic switch in between O and T populations in vivo could contribute to virulence outcome. Similar to the in vivo data disclosed herein, T switched to about 50% opaque. The T population, however, was observed in the mice infected with 1645 over-expressor strains, demonstrating overexpressed 1645 is capable to lock the cells at T phase in vivo. Thus, these data demonstrate that ABUW_1645 is a global regulator controlling virulence.

Based the results above, it was hypothesized that the high attenuation of 1645 over-expressor strains in mice would be attributed by the phenotypic switch in between opaque and translucent populations in vivo. Moreover, 1645 overexpressor strain does not cause lethal infection in mice. Overexpression of 1645 completely abrogated virulence and it was hypothesized that the mice infected with attenuated O/1645 might be protecting against subsequent lethal challenge. To test this, mice were vaccinated intranasally. The vaccinated mice were challenged with the virulent opaque subpopulation 30 days later. PBS controlled mice rapidly succumbed to a challenge on day 2, whilst mice vaccinated with O/1645 were completely protected over a period of ten days. In sum, vaccination with an engineered locked avirulent strain protects mice from lethal challenge with virulent strain.

Taken together, the data highlights the roles of phenotypically diverse *A. baumannii* subpopulations in the progression of disease. The results show that the virulent O subpopulation is dominantly found in the bloodstream of human patients, increasing the risk of spreading the virulent form in the hospital. Furthermore, the O subpopulation is resistant to hospital-used disinfectants and can survive on dry surfaces. This scenario is particularly alarming and worrisome as the hospital may serve as a reservoir to *A. baumannii* virulent subpopulations, circulating in between the patients, healthcare staff and the hospital environment, increasing the risk of hospital-acquired infections. These data disclosed herein shows how the knowledge of the regulatory mechanisms controlling such phenotypic switches can be harnessed to attenuate bacteria and develop translational interventions.

Example 2: A High-Frequency Phenotypic Switch Links Bacterial Virulence and Environmental Survival in *Acinetobacter baumannii*

As described herein, the increasingly pathogenic and antibiotic resistant pathogen, *Acinetobacter baumannii*, harbors a highly virulent subpopulation of cells responsible for disease. This phenotypic subpopulation is resistant to host antimicrobials, which drive its enrichment during infection. Importantly, bacteria harvested from the bloodstream of human patients belong to this virulent subpopulation. Furthermore, the virulent form exhibits increased resistance to hospital disinfectants and desiccation, indicating a role in environmental persistence and the epidemic spread of disease. As disclosed herein, a transcriptional "master regulator" of the switch was identified between avirulent and virulent cells, and whose overexpression abrogated virulence. Further, the overexpression strain vaccinated mice against lethal challenge. This phenotypic subpopulation of bacteria alters the outcome of infection, and illustrates how knowledge of the regulatory mechanisms controlling such phenotypic switches can be harnessed to attenuate bacteria and develop translational interventions.

Figure 5A:
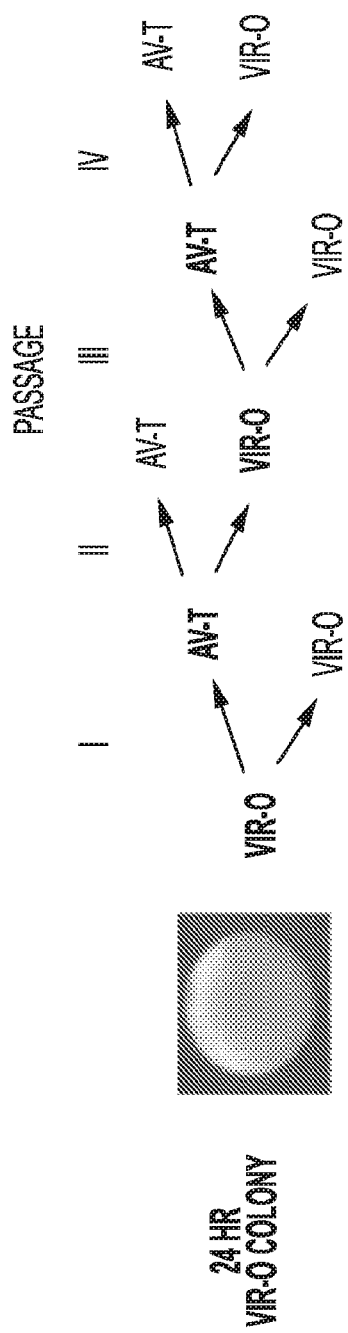
FIGS. 5A-C show switching frequencies between VIR-O (red) and AV-T (blue) from a 24 hour colony.
Figure 5C:
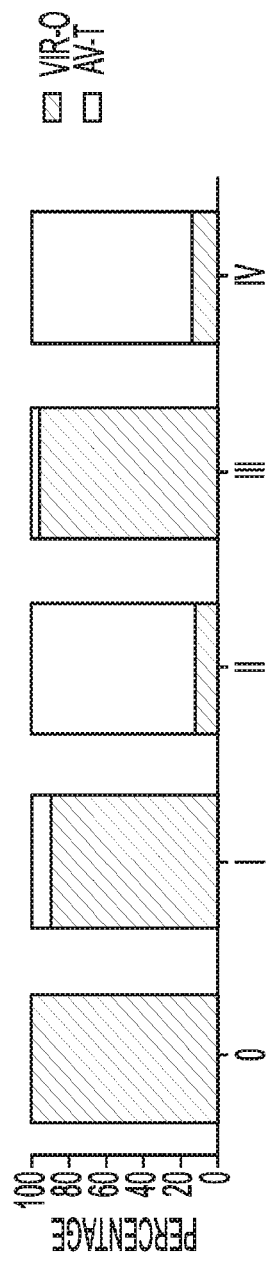
Figure 5B:
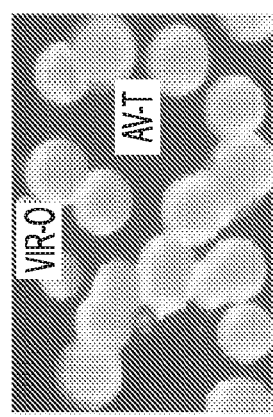
Figure 6:
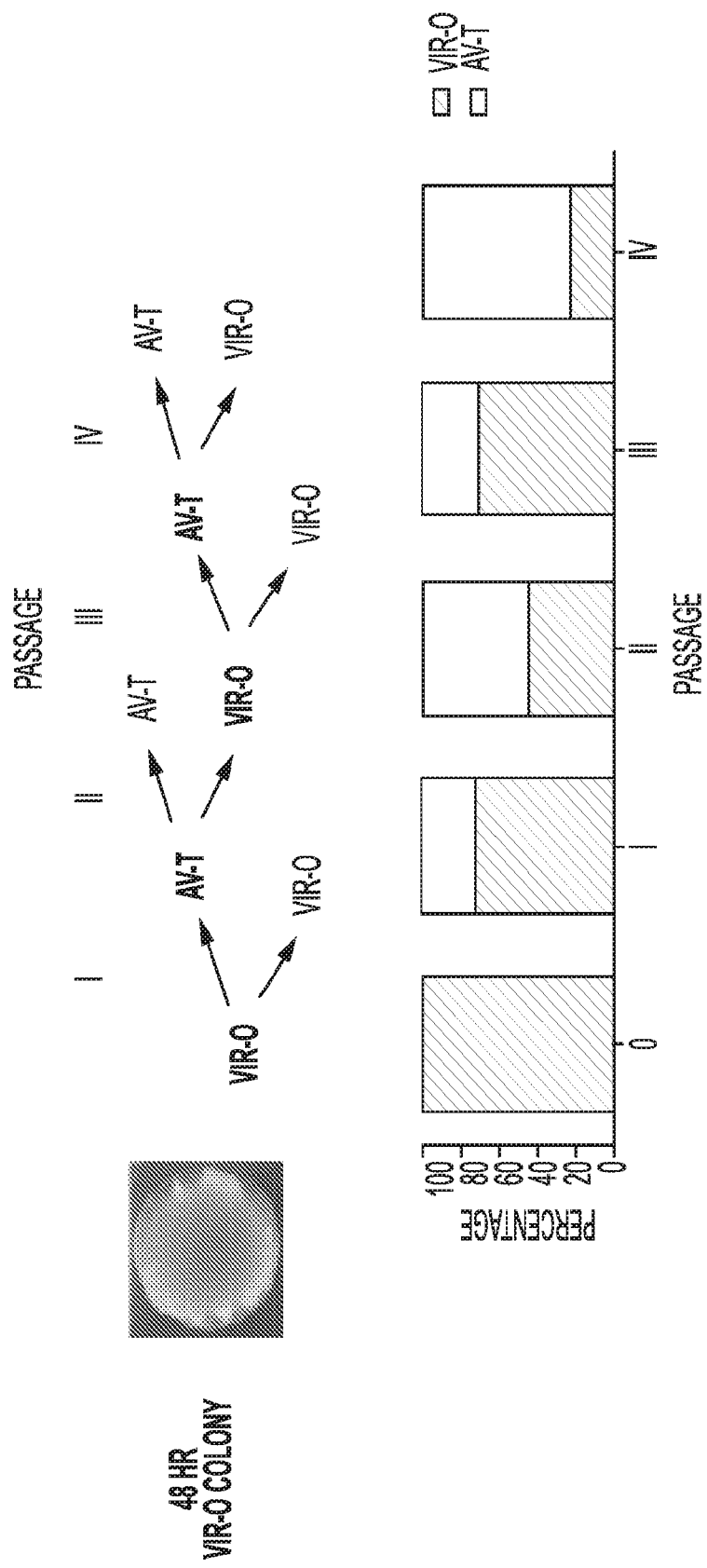
FIG. 6 shows the switching frequencies between VIR-O (red) and AV-T (blue) from a 48 hour colony. Switching frequencies were determined as described in FIG. 5.

Bacteria can exhibit genotypic and/or phenotypic heterogeneity, the latter being traits expressed by some cells within a genetically homogenous population. Characterization of the highly virulent *A. baumannii* isolate (Jacobs, A. C. et al. mBio 5 (2014)) revealed that it exhibits phenotypic heterogeneity by rapidly interconverting between cells capable of forming opaque or translucent (Tipton, K. A., Dimitrova, D. & Rather, P. N. Journal of bacteriology 197, 2593-2599 (2015)) (FIG. 1A). A single colony can be sequentially propagated between opaque and translucent states with switching frequencies of ~4-13% in 24 hr colonies (FIG. 5) and 20-40% in 48 hr colonies (FIG. 6). A high degree of AV-T sectors were observed. It was thought that differences in capsule contributed to the opacity differences between VIR-O and AV-T cells. Examination of cells by electron microscopy after staining for capsule with ruthenium red revealed the VIR-O cells produced a capsule with a 2-fold increased thickness compared to that of AV-T cells (FIGS. 1B and 1C). By comparison, VIR-O and AV-T cells missing the Wzc tyrosine kinase required for capsule synthesis (Δwzc) failed to produce any capsular material and exhibited a translucent phenotype that was more pronounced than the AV-T cells (Geisinger, E. & Isberg, R. R. PLoS pathogens 11, (2015)).

The roles of these two phenotypic subpopulations in the progression of disease are unclear. After intranasal inoculation of mice with a 1:1 mixture of the two types of cells, the cells that form opaque colonies (VIR-O; virulent, opaque) vastly outcompeted those that form translucent colonies (AV-T cells; avirulent, translucent) in the organs tested (lungs, spleen, liver) at 24 hours post-infection (h.p.i.) (FIG. 1D). Similar results were obtained in single infection experiments where mice infected with VIR-O cells harbored over 10,000-fold more bacteria in the lungs than mice infected with AV-T cells (FIG. 1E). In addition, 1,000-fold more bacteria were recovered in the spleens and livers of the VIR-O-infected mice than those infected with AV-T cells (FIG. 7). Surprisingly, while bacteria recovered from VIR-O-infected mice remained in the VIR-O form (FIG. 1F; At 24 hours post-infection, organs were harvested and plated to assess the percentage of VIR-O and AV-T cells present), there was a greater than 3,000-fold increase in the frequency of VIR-O cells recovered from the AV-T-infected mice, as compared to the inoculum (0.01% VIR-O cells in the inoculum of AV-T-infected mice) (FIG. 1G). Presented data were pooled from two separate experiments and repeated at least 10 times. At 24 hours post-infection, lungs were harvested and plated for colony forming units (e). Furthermore, VIR-O cells derived from AV-T colonies regained virulence in mice (FIG. 8), confirming that the attenuation of AV-T cells was not due to random mutations within the genome. These results revealed a strong selective pressure for the VIR-O population in vivo. In survival experiments, VIR-O-infected mice rapidly succumbed to disease by day 2, whereas AV-T infected-mice survived (FIG. 1H). Taken together, these data indicate that the VIR-O population is virulent and predominates during in vivo infection, whereas the AV-T population is unable to cause acute disease.

It was unclear which factors were responsible for the enrichment of the VIR-O population following in vivo lung infection (FIG. 1E). The lung is replete with innate immune antimicrobials including lysozyme, antimicrobial peptides such as CRAMP, and reactive oxygen species (Geisinger, E. & Isberg, R. R. PLoS pathogens 11 (2015); and Martin, T. R. & Frevert, C. W. Proceedings of the American Thoracic Society 2, 403-411 (2005)). It was thought that the VIR-O cells might be more resistant than AV-T to such antimicrobials. To test this, time-kill assays with hydrogen peroxide (which leads to the generation of reactive oxygen species), lysozyme, and CRAMP were conducted. After 1 hour of treatment with each of the three antimicrobials, VIR-O cells vastly outnumbered AV-T cells (FIG. 2A). Moreover, VIR-O cells also outnumbered AV-T after treatment with LL-37, the human orthologue of CRAMP (FIG. 10). These data highlight that VIR-O cells are more resistant than AV-T cells to diverse innate immune antimicrobials.

Figure 11:
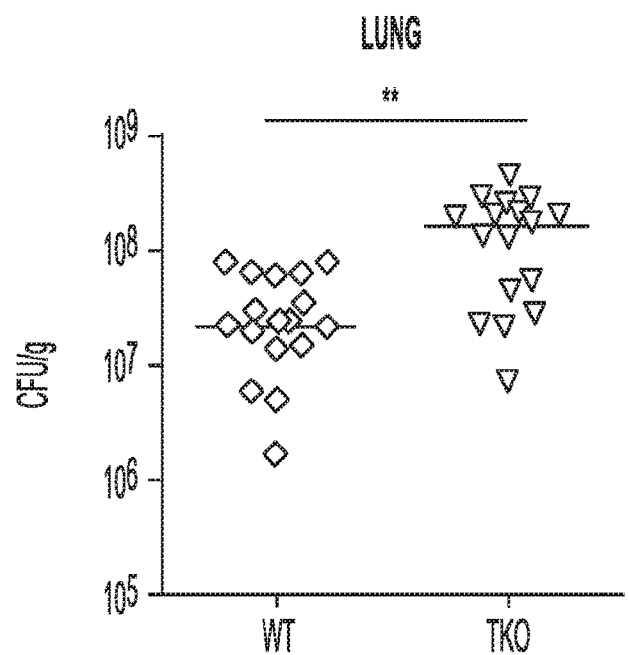
FIG. 11 shows that triple knockout mice lacking antimicrobials exhibit increased bacterial levels during AV-T infection. Wild-type (WT, black) or triple knockout (TKO; red) mice lacking the gp91 subunit of the NADPH oxidase, lysozyme and CRAMP were infected with AV-T. At 8 h.p.i, lungs were harvested and plated for CFU enumeration. Error bars represent geometric mean and Mann-Whitney test (**p<0.005).

To test whether these host defenses contributed to the enrichment of the VIR-O subpopulation during in vivo infection, wild-type (WT) mice and triple knockout (TKO) mice lacking a functional NADPH oxidase (cybb$^{-/-}$; required for the production of reactive oxygen species), CRAMP (cramp$^{-/-}$), and lysozyme (lysM$^{-/-}$) were infected with an inoculum of AV-T cells. At 8 hours post-infection, lungs were harvested and plated to assess the percentage of VIR-O cells present. Presented data were pooled from three separate experiments and repeated at least 5 times for a total of 18-23 mice/per group. Also, at 8 hr post-infection, lungs from WT mice harbored a higher percentage of VIR-O cells than those from TKO mice (FIG. 2B). This was despite the overall levels of bacteria being higher in TKO mice than WT mice (FIG. 11). These data indicate that reactive oxygen species, CRAMP, and lysozyme specifically contribute to the enrichment of the virulent VIR-O subpopulation during early infection. However, since the VIR-O population is still enriched in the TKO mice, this indicates that other host factors are involved as well.

Since the VIR-O subpopulation displayed increased resistance to host-derived antimicrobials, cells were examined to test for resistance to hospital disinfectants. The VIR-O and AV-T subpopulations were tested for sensitivity to three of the most commonly used disinfectants; benzethonium chloride (BZT), benzalkonium chloride (BAK) and chlorhexidine gluconate (CHG); and the VIR-O cells displayed increased resistance to the three agents compared to the AV-T cells (FIGS. 2C-E). In addition to resistance to disinfectants, desiccation resistance is a major contributor to the persistence of A. baumannii in the hospital environment. Following eight days of desiccation, VIR-O cells survived better on dry surfaces compared to AV-T cells (FIG. 2F). Moreover, while viable bacteria recovered from VIR-O cells remained in the VIR-O form (FIG. 2G), there was a greater than 5,000-fold increase in the frequency of VIR-O cells recovered from the desiccated AV-T cells (FIG. 2H). Taken together, these data link increased virulence and environmental persistence (resistance to hospital disinfectants and desiccation) to a single phenotypic subpopulation of bacterial cells.

Figure 12:
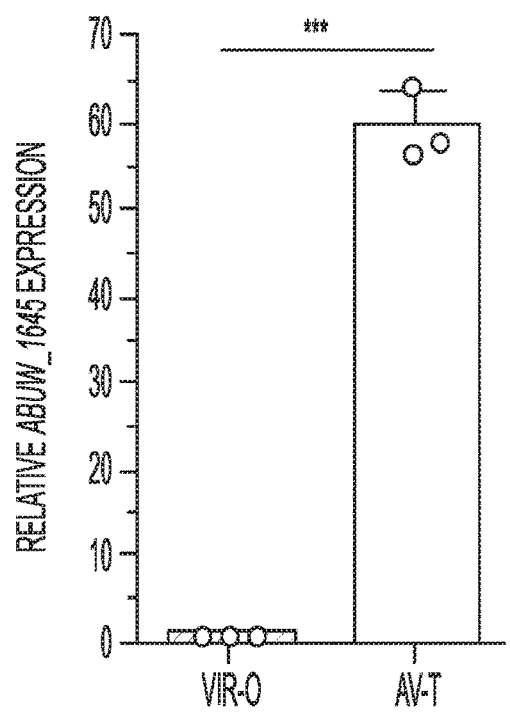
FIG. 12 shows AV-T cells express higher levels of ABUW_1645. RNA was harvested from Error bars represent standard deviation of the mean.
Figures 13A, 13B:
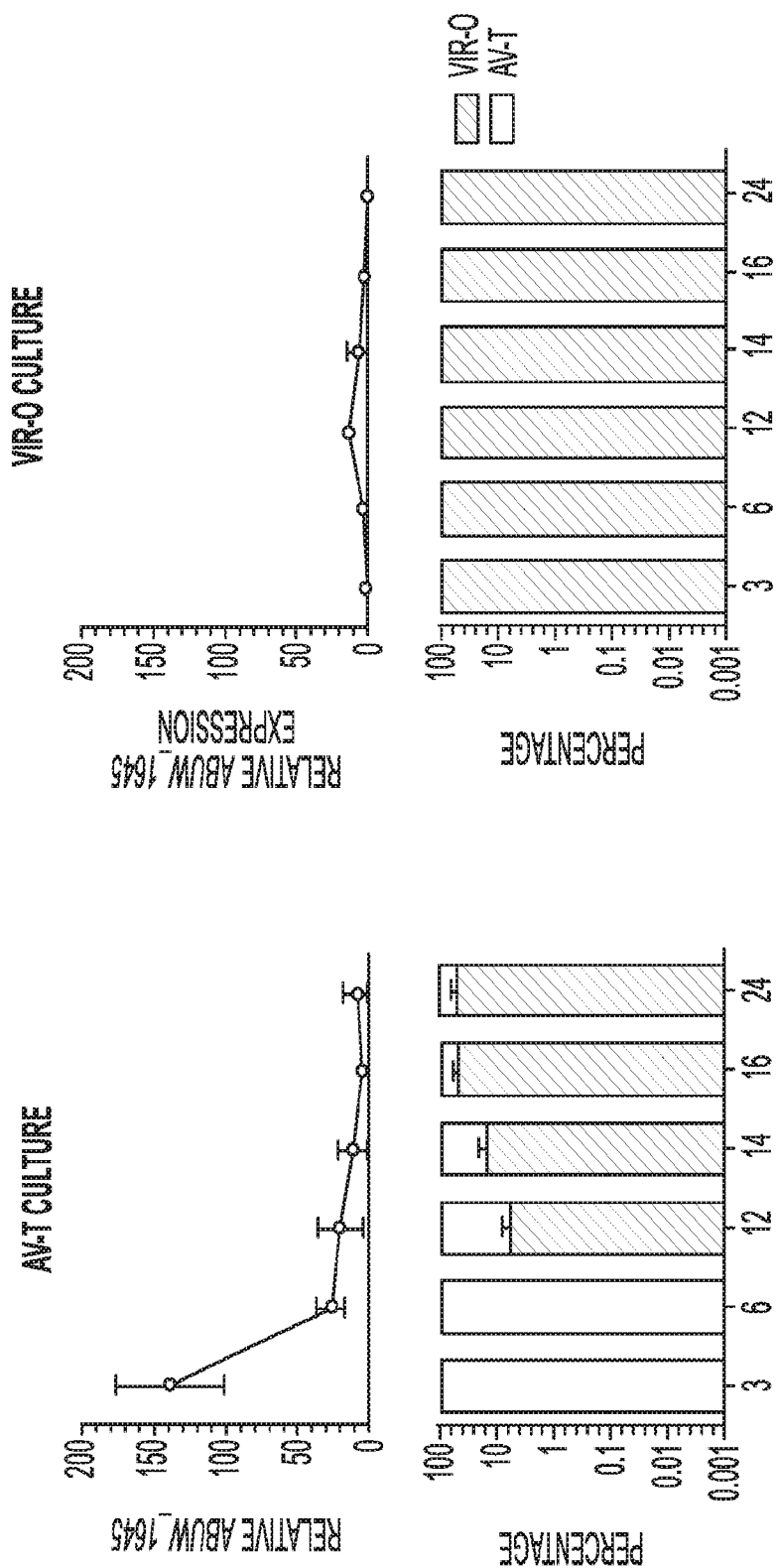
FIGS. 13A-B show that ABUW_1645 expression correlates with phenotypic VIR-O and AV-T switch. RNA was harvested from (A) AV-T and (B) VIR-O cultures over the course of 24 hours and used for quantitative real time analysis of ABUW_1645 expression in relative to the housekeeping 16s rRNA. At each time point, cultures were plated to assess for the percentage of VIR-O and AV-T cells present.
Figure 16A:
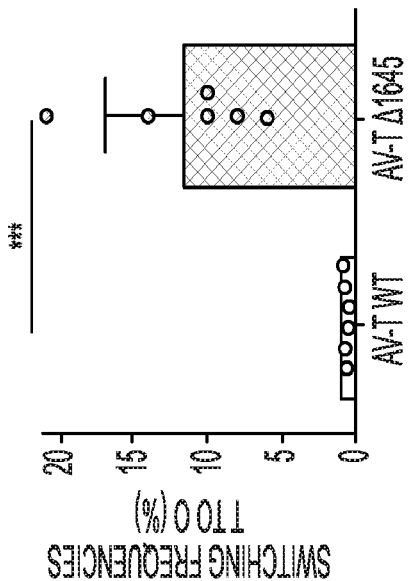
FIGS. 16A-B show the switching frequencies of the wild-type and the 1645 mutant from VIR-O to AV-T (FIG. 16A) or AV-T to VIR-O (FIG. 16B).
Figure 16B:
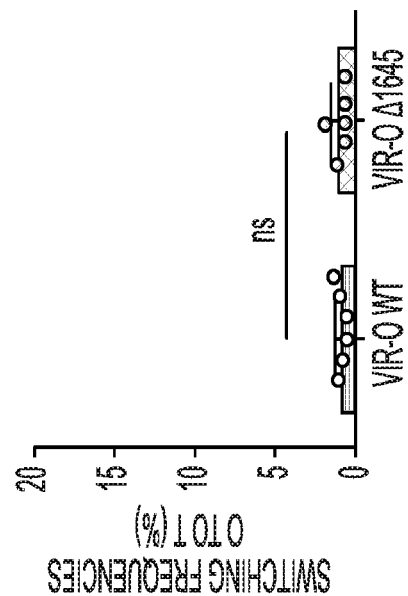

To elucidate factors controlling the virulent VIR-O and avirulent AV-T subpopulations, genome-wide transcriptional profiling was performed. RNA-seq revealed that a predicted TetR-type transcriptional regulator, ABUW_1645 (or "1645"), was among the most differentially expressed regulatory genes between the VIR-O and AV-T subpopulations (Table 1). qRT-PCR confirmed that the AV-T population expressed approximately 50-fold higher levels of 1645 as compared to VIR-O cells (FIG. 12; AV-T and VIR-O cultures were used for quantitative real time analysis of ABUW_1645 expression relative to the housekeeping 16s rRNA). Intriguingly, ABUW_1645 expression was reduced significantly as AV-T cells gradually switched to VIR-O (FIG. 13A), whereas its expression level in the opaque cells remained low (FIG. 13B). An in-frame deletion of ABUW_1645 did not alter the rate of VIR-O to AV-T switching, but the rate of AV-T to VIR-O switching was increased 18-fold relative to wild-type, indicating a role for ABUW_1645 in maintaining the AV-T state (FIG. 16).

TABLE 1

Differential expressed genes in AV-T relative to VIR-O.

| Feature.ID | Gene name | Gene function | p.Value | FDR | LFC (AV-T/vector vs VIR-O/vector |
| --- | --- | --- | --- | --- | --- |
| ABUW_2818* | — | TetR family transcriptional regulator | 2.00157E−61 | 7.73808E−58 | 4.915216955 |
| ABUW_1645 | — | transcriptional regulator, TetR family | 9.0716E−18 | 1.75354E−14 | 2.301672048 |
| ABUW_2408* | — | LrgA family protein | 0.000621503 | 0.024683794 | 1.708356159 |
| ABUW_0143 | — | TonB-dependent receptor protein | 1.82002E−06 | 0.000180415 | 1.457183349 |
| ABUW_0904 | — | alkaline phosphatase | 4.89709E−08 | 8.23136E−06 | 1.371783697 |
| ABUW_0813* | — | hypothetical protein | 1.90732E−07 | 2.83604E−05 | 1.370619141 |
| ABUW_2921* | — | formylglycine-generating sulfatase enzyme domain-containing protein | 1.42528E−05 | 0.001039646 | 1.365134692 |
| ABUW_2696 | — | #N/A | 9.15688E−07 | 0.000104119 | 1.236190442 |
| ABUW_2122* | — | oxidoreductase | 5.37233E−05 | 0.003245224 | 1.226512802 |
| ABUW_1044* | — | hypothetical protein | 2.6963E−05 | 0.001828751 | 1.176246145 |
| ABUW_0812 | — | hypothetical protein | 7.59706E−06 | 0.000638483 | 1.131448712 |
| ABUW_3403 | — | TonB-dependent receptor | 0.000129836 | 0.00664769 | 1.0991632 |
| ABUW_0070 | fahA | fumarylacetoacetase | 0.00012879 | 0.00664769 | 1.046470806 |
| ABUW_0066 | hppD | 4-hydroxyphenylpyruvate dioxygenase | 0.000258734 | 0.011767811 | 1.040780318 |
| ABUW_0068 | — | glyoxalase/bleomycin resistance protein/dioxygenase | 0.000516423 | 0.021701013 | 1.040300808 |
| ABUW_0651* | — | RtcB family protein | 7.36291E−05 | 0.004248508 | 1.010368124 |
| ABUW_0810* | — | hypothetical protein | 0.001145239 | 0.039531197 | 0.992285043 |
| ABUW_0566 | — | phage-related major tail tube protein (FII-like) | 0.001323641 | 0.045284938 | 0.986078588 |
| ABUW_0337* | mdfA | chloramphenicol resistance pump cmr | 8.42617E−05 | 0.004648711 | 0.979928548 |
| ABUW_1660* | — | ABC transporter, ATP-binding protein | 9.29778E−05 | 0.004924001 | 0.965603901 |
| ABUW_3125 | bfr2 | bacterioferritin | 0.000244548 | 0.011255024 | 0.918564326 |
| ABUW_0381 | — | DEAD/DEAH box helicase | 0.000435939 | 0.018520206 | 0.884457817 |

TABLE 1-continued

Differential expressed genes in AV-T relative to VIR-O.

| Feature.ID | Gene name | Gene function | p.Value | FDR | LFC (AV-T/vector vs VIR-O/vector |
|---|---|---|---|---|---|
| ABUW_4057 | aadA1 | aminoglycoside 3″-adenylyltransferase aadA1 | 0.000220021 | 0.010501268 | 0.855683002 |
| ABUW_2923 | — | hypothetical protein | 0.001489161 | 0.049630133 | −0.778440897 |
| ABUW_3579 | — | hypothetical protein | 0.001365307 | 0.046300687 | −0.803105363 |
| ABUW_1210 | — | hypothetical protein | 0.0006558 | 0.025609318 | −0.817472718 |
| ABUW_2436 | katE | catalase | 0.0009055 | 0.03302513 | −0.839692432 |
| ABUW_0259 | — | sulfate transporter | 0.000780385 | 0.029870979 | −0.840947021 |
| ABUW_2578 | — | type VI secretion system effector, Hcp1 family | 0.00104175 | 0.036282946 | −0.845669728 |
| ABUW_0053 | — | UPF0391 membrane protein | 0.000951801 | 0.034070941 | −0.854295085 |
| ABUW_1027 | degP | peptidase S1C, Do | 0.000898922 | 0.03302513 | −0.871637245 |
| ABUW_1194* | ampC | beta-lactamase ADC7 | 0.000228413 | 0.010702181 | −0.878944874 |
| ABUW_2554 | — | putative hemolysin | 0.000267875 | 0.012041935 | −0.882858345 |
| ABUW_1128* | — | hypothetical protein | 0.000214522 | 0.010366798 | −0.894814047 |
| ABUW_1536 | — | hypothetical protein | 0.000868123 | 0.032270817 | −0.903293993 |
| ABUW_1499 | — | EamA-like transporter family protein | 0.000625714 | 0.024683794 | −0.911893193 |
| ABUW_0944 | — | oxidoreductase alpha (molybdopterin) subunit | 0.000229767 | 0.010702181 | −0.918789675 |
| ABUW_1076* | — | hypothetical protein | 0.000343403 | 0.014916789 | −0.922651828 |
| ABUW_1227 | — | acyl-CoA dehydrogenase | 0.000191926 | 0.009392229 | −0.924010289 |
| ABUW_3346 | acnA | aconitate hydratase 1 | 0.000322586 | 0.014171773 | −0.926969624 |
| ABUW_2832 | — | hypothetical protein | 0.000547423 | 0.022514245 | −0.938225273 |
| ABUW_2639 | — | universal stress protein family | 9.18696E-05 | 0.004924001 | −0.953993334 |
| ABUW_2519* | — | hypothetical protein | 0.00146342 | 0.049196361 | −0.965956612 |
| ABUW_0274 | — | PGAP1-like GPI inositol-deacylase | 0.001037545 | 0.036282946 | −0.966124285 |
| ABUW_0116 | — | Gp5 domain-containing protein | 0.000170236 | 0.008437617 | −0.980194072 |
| ABUW_0851 | — | hypothetical protein | 8.48337E-05 | 0.004648711 | −0.987633118 |
| ABUW_1473 | — | hypothetical protein | 8.37965E-05 | 0.004648711 | −1.001629876 |
| ABUW_0237* | aqpZ | aquaporin Z | 3.46778E-05 | 0.002208772 | −1.01379071 |
| ABUW_2058 | — | hypothetical protein | 3.43611E-05 | 0.002208772 | −1.018109436 |
| ABUW_1905 | — | isochorismatase hydrolase | 0.000925303 | 0.03343198 | −1.023763987 |
| ABUW_1287 | — | hypothetical protein | 0.000423817 | 0.018205288 | −1.026620022 |
| ABUW_2161 | — | hypothetical protein | 6.68332E-05 | 0.003914803 | −1.047486814 |
| ABUW_0646 | — | glycosylase/bleomycin resistance/fosfomycin resistance/dioxygenase domain-containing protein | 3.62431E-05 | 0.002259933 | −1.069574174 |
| ABUW_1693 | — | heme oxygenase-like protein | 3.14713E-05 | 0.002097724 | −1.074141993 |
| ABUW_2933 | — | aldose 1-epimerase | 1.09314E-05 | 0.00081271 | −1.079884798 |
| ABUW_2074 | — | transcriptional regulator, fur family | 0.00055774 | 0.022697063 | −1.089615925 |
| ABUW_3106 | — | peptidoglycan-binding LysM | 9.62513E-06 | 0.000759403 | −1.09479475 |
| ABUW_2834 | — | hypothetical protein | 0.000164822 | 0.008275359 | −1.108357881 |
| ABUW_0117 | — | hypothetical protein | 3.48513E-05 | 0.002208772 | −1.121926699 |
| ABUW_3515 | cbpA | curved DNA-binding protein | 5.01358E-06 | 0.000450756 | −1.130234332 |
| ABUW_2725* | gst | glutathione S-transferase | 9.88949E-06 | 0.000764656 | −1.135099295 |
| ABUW_0181 | — | hypothetical protein | 5.6864E-06 | 0.000488989 | −1.143888233 |
| ABUW_1573* | — | acyl-CoA dehydrogenase | 8.53747E-05 | 0.004648711 | −1.152675852 |
| ABUW_0771 | — | hypothetical protein | 4.82149E-05 | 0.002958711 | −1.153686976 |
| ABUW_1471 | ygiW2 | bacterial OB fold domain-containing protein YgiW | 0.000995262 | 0.035299859 | −1.159158709 |
| ABUW_3026 | — | glyoxalase | 8.63077E-06 | 0.000709927 | −1.172701199 |
| ABUW_0233 | — | hypothetical protein | 3.18305E-06 | 0.000300138 | −1.181108957 |
| ABUW_0121 | — | bacterial SH3 domain-containing protein | 8.82763E-06 | 0.000710992 | −1.191835384 |
| ABUW_1572* | — | short-chain dehydrogenase/reductase | 6.3764E-05 | 0.003792488 | −1.217300799 |
| ABUW_2455* | — | methylcrotonoyl-CoA carboxylase subunit alpha | 3.85554E-07 | 5.13984E-05 | −1.226698819 |
| ABUW_2454 | mgh | 3-methylglutaconyl-CoA hydratase | 1.157E-06 | 0.000124249 | −1.237259797 |
| ABUW_3865* | — | putative flavoprotein | 7.33725E-07 | 8.5957E-05 | −1.240961448 |
| ABUW_2435 | — | oxidoreductase | 0.000567874 | 0.022868744 | −1.255140213 |
| ABUW_2730 | — | OmpA/MotB | 6.90049E-07 | 8.33666E-05 | −1.257349861 |
| ABUW_2450* | — | long-chain fatty-acid-CoA ligase | 3.39718E-06 | 0.000312702 | −1.28090319 |
| ABUW_0118 | — | hypothetical protein | 5.39471E-07 | 6.72772E-05 | −1.285871348 |

TABLE 1-continued

Differential expressed genes in AV-T relative to VIR-O.

| Feature.ID | Gene name | Gene function | p.Value | FDR | LFC (AV-T/vector vs VIR-O/vector) |
|---|---|---|---|---|---|
| ABUW_1282* | — | hypothetical protein | 2.28442E−05 | 0.001577069 | −1.293825891 |
| ABUW_1902 | sndH2 | L-sorbosone dehydrogenase | 1.8151E−06 | 0.000180415 | −1.304365804 |
| ABUW_1652 | — | hypothetical protein | 0.000531301 | 0.022086111 | −1.338203834 |
| ABUW_1633 | — | fimbrial biogenesis outer membrane usher protein | 1.21368E−06 | 0.000126813 | −1.353270987 |
| ABUW_2061 | — | hypothetical protein | 5.38832E−07 | 6.72772E−05 | −1.387516291 |
| ABUW_1903 | — | hypothetical protein | 2.21509E−05 | 0.00155701 | −1.393659853 |
| ABUW_2451 | — | transcriptional regulator AcrR family | 1.47928E−08 | 3.00994E−06 | −1.437296542 |
| ABUW_2685 | — | hypothetical protein | 0.000829729 | 0.031391036 | −1.444745708 |
| ABUW_2686 | — | hypothetical protein | 3.83784E−07 | 5.13984E−05 | −1.449387973 |
| ABUW_2456* | — | hydroxymethylglutaryl-CoA lyase | 2.66266E−08 | 4.90183E−06 | −1.458717146 |
| ABUW_2691 | — | transporter LysE family | 1.06064E−06 | 0.000117155 | −1.467473995 |
| ABUW_3217 | add2 | adenosine deaminase | 6.27873E−08 | 1.0114E−05 | −1.489326388 |
| ABUW_2684 | — | phage putative head morphogenesis protein | 0.000130684 | 0.00664769 | −1.49891424 |
| ABUW_2065 | — | hypothetical protein | 1.17389E−08 | 2.52126E−06 | −1.518525474 |
| ABUW_3352 | — | putative transcriptional regulator | 1.70005E−10 | 5.97491E−08 | −1.587382829 |
| ABUW_3147 | — | hypothetical protein | 4.70767E−10 | 1.39999E−07 | −1.598364095 |
| ABUW_1988 | — | hypothetical protein | 1.95743E−05 | 0.001401376 | −1.598822306 |
| ABUW_2452* | — | isovaleryl-CoA dehydrogenase | 7.67693E−11 | 2.9679E−08 | −1.622826603 |
| ABUW_2060 | — | hypothetical protein | 3.48552E−09 | 8.90173E−07 | −1.643082209 |
| ABUW_2453* | — | methylcrotonoyl-CoA carboxylase beta chain | 4.64403E−11 | 1.99487E−08 | −1.6473942 |
| ABUW_1508 | — | lipocalin family protein | 0.00071735 | 0.027732752 | −1.661588713 |
| ABUW_2149 | — | hypothetical protein | 5.6918E−06 | 0.000488989 | −1.684595935 |
| ABUW_1632 | — | PapD-like P pilus assembly protein | 3.68411E−09 | 8.90173E−07 | −1.82504609 |
| ABUW_2621 | — | hypothetical protein | 2.78073E−10 | 8.9586E−08 | −1.831083983 |
| ABUW_2442 | — | hypothetical protein | 1.85524E−08 | 3.58618E−06 | −1.832438149 |
| ABUW_0328 | — | hemerythrin | 1.13383E−11 | 5.47926E−09 | −1.837037338 |
| ABUW_0235 | — | transporter LysE family | 2.5523E−07 | 3.65452E−05 | −1.841394326 |
| ABUW_1467 | — | acyl-CoA dehydrogenase | 1.60953E−07 | 2.48897E−05 | −1.856545115 |
| ABUW_1286 | — | hypothetical protein | 2.99821E−06 | 0.000289777 | −1.861413285 |
| ABUW_0628 | — | peroxidase | 1.47223E−12 | 8.13092E−10 | −1.916796142 |
| ABUW_3351 | — | heme oxygenase-like protein | 4.55045E−15 | 3.51841E−12 | −2.010990393 |
| ABUW_3122 | otsB | trehalose-phosphatase | 0.000299831 | 0.013323531 | −2.06556065 |
| ABUW_1651 | — | hypothetical protein | 3.36154E−08 | 5.90714E−06 | −2.129653059 |
| ABUW_1659 | — | hypothetical protein | 9.75446E−09 | 2.21828E−06 | −2.157222364 |
| ABUW_2673 | — | hypothetical protein | 1.35141E−11 | 8.13092E−10 | −2.179770653 |
| ABUW_2064 | — | hypothetical protein | 1.48781E−09 | 4.10849E−07 | −2.208853253 |
| ABUW_2434 | — | hypothetical protein | 1.02331E−05 | 0.000775712 | −2.226155348 |
| ABUW_1631 | — | spore coat protein U | 1.62046E−16 | 1.56618E−13 | −2.252388237 |
| ABUW_2861* | — | hypothetical protein | 0.000836336 | 0.031391036 | −2.348140035 |
| ABUW_1466 | — | hypothetical protein | 4.30817E−17 | 5.55179E−14 | −2.58878957 |

*indicates ABUW_1645-regulated genes.

Figures 3A, 3B, 3C:
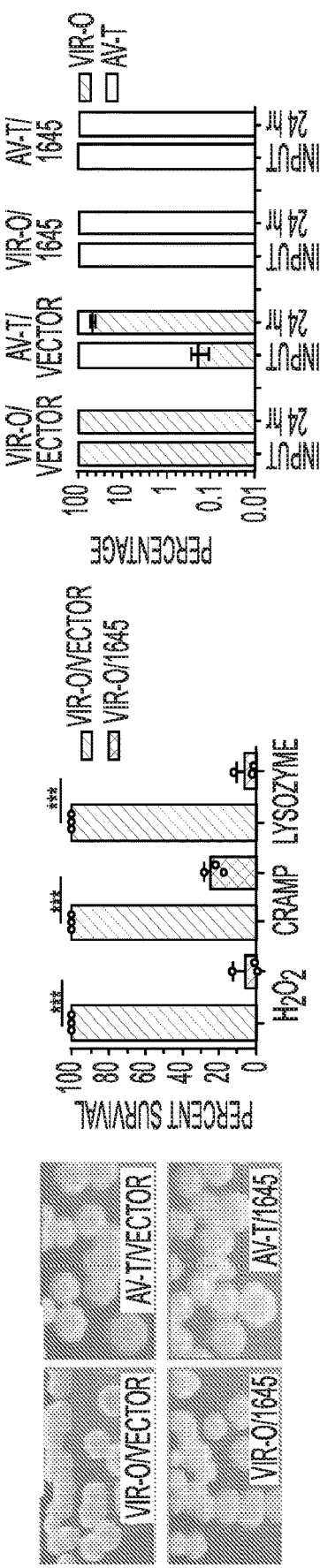

Strikingly, overexpression of 1645 in VIR-O cells (VIR-O/1645) led to a translucent colony morphology, and a complete inability to switch back to VIR-O (FIG. 3A). AV-T cells overexpressing 1645 (AV-T/1645) were similarly "locked", and unable to switch to VIR-O cells (FIG. 3A). Transcriptional profiling of VIR-O/vector and VIR-O/1645 cells revealed that 1645 controlled ~70% of the genes differentially expressed between the VIR-O and AV-T cells (Table 1). Taken together, these data identify 1645 as a master regulator of the VIR-O/AV-T high frequency phenotypic switch.

Figure 15A:
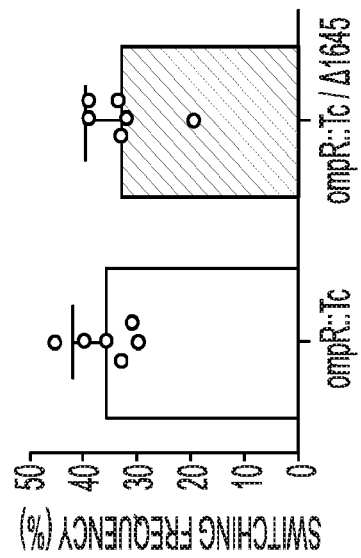
FIGS. 15A-B shows OmpR and 1645 regulate VIR-O to AV-T switching by separate pathways.
Figure 15B:
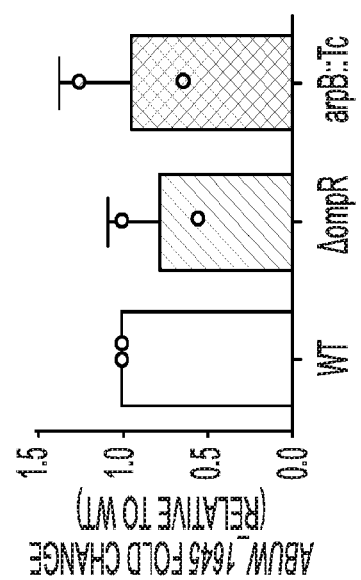

Previously identified mutations that either increased (ompR) (Tipton, K. A. & Rather, P. N. Journal of bacteriology (2016)) or decreased (arpB) (Tipton, K. A., Farokhyfar, M. & Rather, P. N. Microbiology Open (2016)) the rate of VIR-O to AV-T switching did not alter ABUW_1645 expression (FIG. 15A). Furthermore, the 1645 deletion did not alter the hyper-switching phenotype of an ompR::Tc mutant (FIG. 15B). In addition, RNA-Seq data indicated that the expression of ompR or arpB was not altered by 1645 overexpression (Table 1). Therefore, ABUW_1645 regulates phenotypic switching by a pathway separate from that regulated by OmpR or ArpB.

Figure 3F:
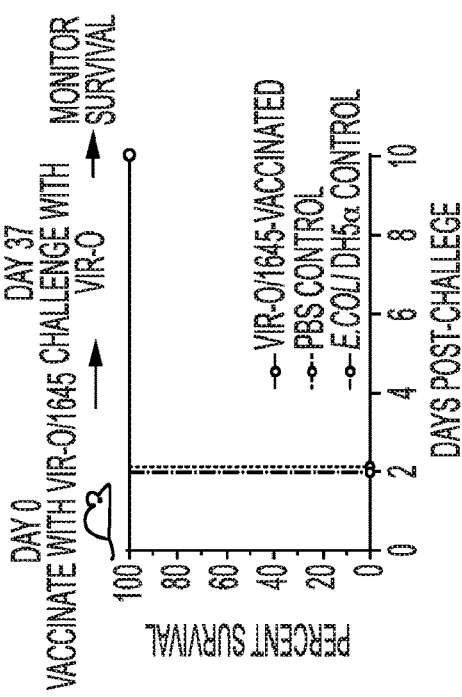
Figure 3F:
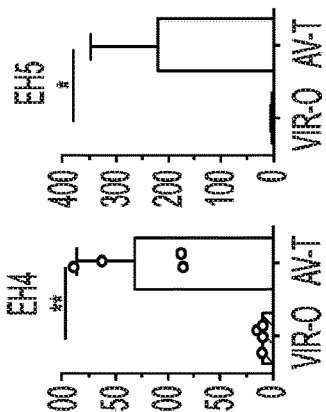
Figure 3E:
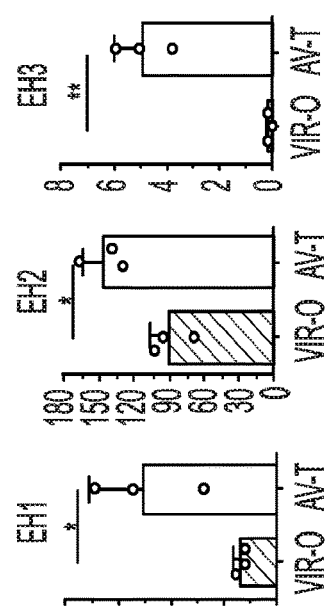
Figure 3E:
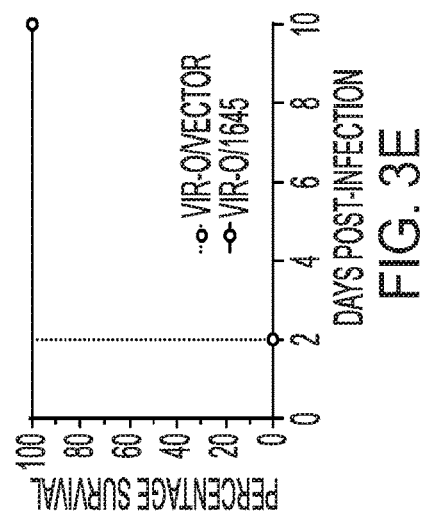
Figure 3D:
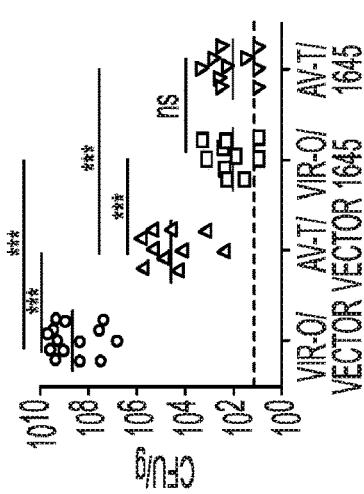
Figure 3G:
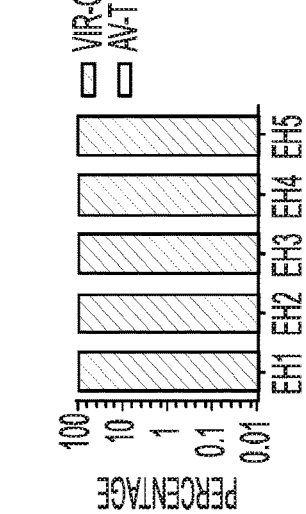
Figure 4B:
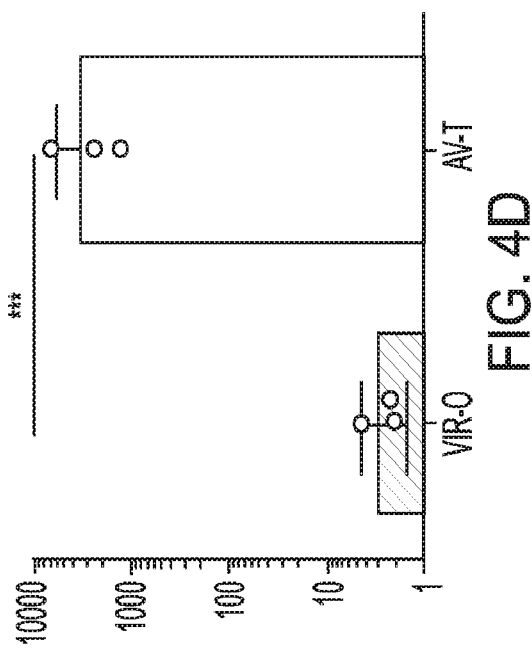
FIGS. 4A-D show AV-T specific phenotypes.
Figure 4D:
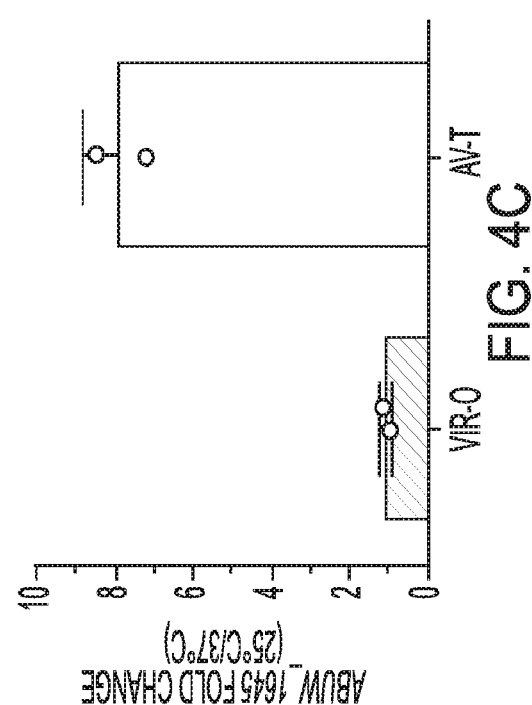
Figure 4A:
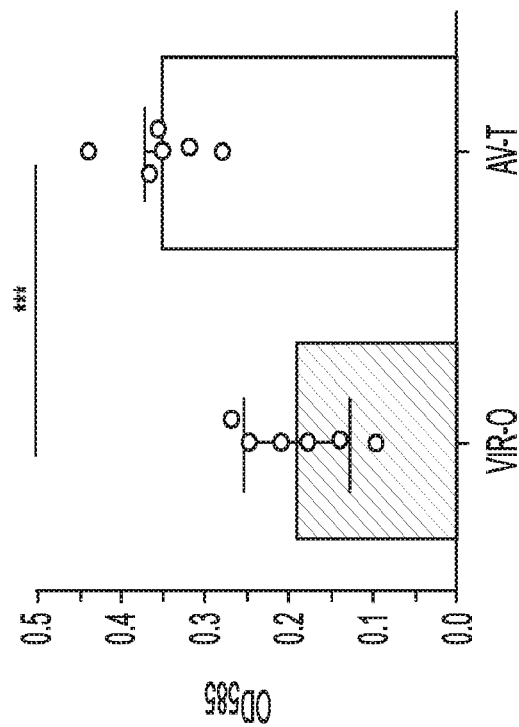
Figure 4C:
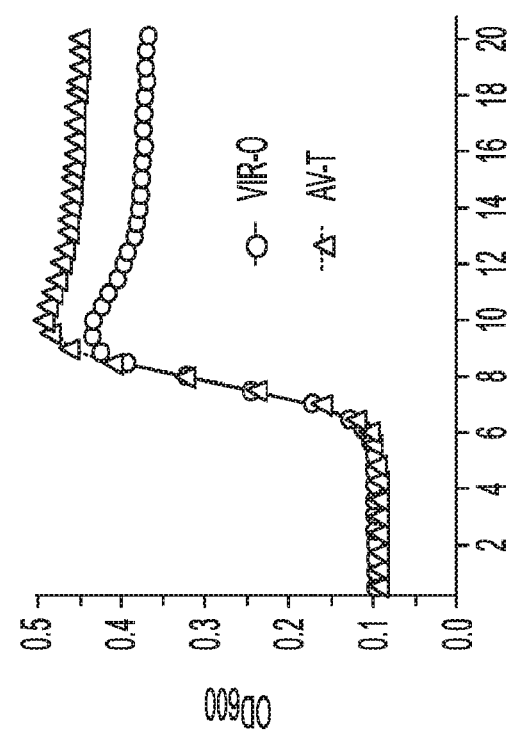
Figure 17:
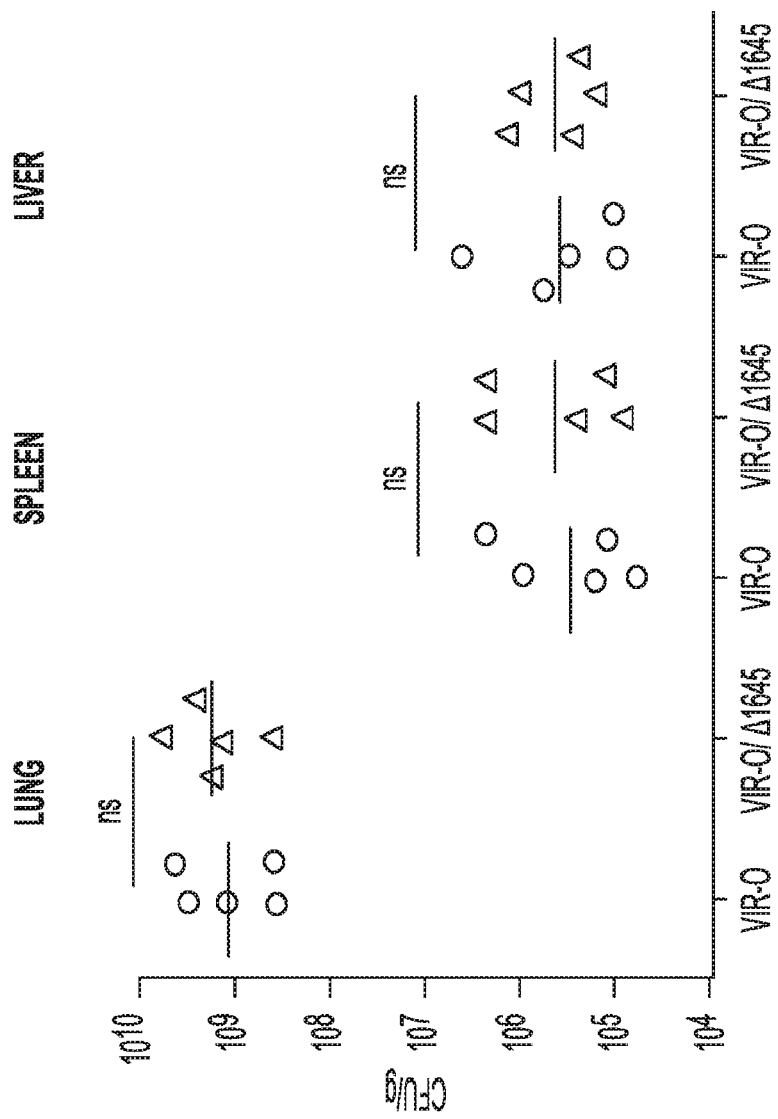
FIG. 17 shows that a deletion of the 1645 gene does not alter virulence in the lung or the ability to generate a systemic infection.

Overexpression of 1645 in VIR-O cells completely reversed resistance to host antimicrobials (FIG. 3B), disinfectants (FIGS. 14A-B) and desiccation (FIGS. 14C-D). In single infection experiments, VIR-O cells were recovered from mice infected with either VIR-O/vector or AV-T/vector cells (FIG. 3C). In contrast, AV-T cells were recovered from mice infected with 1645 overexpression strains (FIG. 3C). This was associated with drastic attenuation of both VIR-O/1645 and AV-T/1645 strains, which exhibited a 7-log reduction in bacterial levels in the lungs relative to VIR-O/vector-infected mice (FIG. 3D). Furthermore, since the 1645 overexpression strains are even less virulent than AV-T cells, these data indicate that the residual colonization of mice during AV-T infection is in fact due to VIR-O cells, which become enriched during infection. This strongly indicates that AV-T cells do not have the ability to replicate and/or survive during in vivo infection, whereas VIR-O cells are responsible for causing disease. In agreement with these findings, infection of mice with the 1645 deletion mutant led to the recovery of VIR-O cells and this strain was not attenuated compared to wild-type (FIG. 17), as was the 1645 overexpression strain. VIR-O/1645 bacteria were unable to cause a lethal infection, as compared to VIR-O/vector cells, which caused a rapidly lethal infection (FIG. 3E). These data highlight 1645 as an important regulator of virulence as well as traits associated with persistence in the hospital environment.

Since the VIR-O/1645 strain was completely attenuated in vivo, it was tested whether it might protect mice against subsequent lethal challenge with the virulent VIR-O/vector cells. While control mice vaccinated with PBS or *Escherichia coli* K-12 rapidly succumbed to challenge on day 2, mice vaccinated with VIR-O/1645 were completely protected (FIG. 3F). These data demonstrate that a strain engineered to be locked to produce avirulent cells can effectively provide protection against otherwise lethal infection, serving as a live attenuated vaccine against *A. baumannii*.

Because VIR-O cells clearly predominate during experimental in vivo murine infection, as well as in conditions that simulate stresses encountered in the hospital environment, their abundance was tested in samples from hospitalized human patients. Blood cultures from 5 patients were directly plated on agar with systemic *A. baumannii* infections, under conditions that prevent switching between VIR-O and AV-T cells. VIR-O cells, and no AV-T cells, were detected from these clinical isolates (FIG. 3G). Therefore, similarly to experimental infections in mice, VIR-O cells vastly predominate in human infections. In addition, AV-T variants could be selected from the VIR-O cells of each clinical isolate, indicating that this phenotypic switch is present in *A. baumannii* isolates other than AB5075. Moreover, the expression of ABUW_1645 was significantly higher in the AV-T subpopulation from each isolate, relative to the corresponding VIR-O subpopulation, further supporting the important role of this regulator in the VIR-O to AV-T switch (FIG. 3H). These results provide clinical evidence from diverse isolates that highlights the important role of the phenotypic subpopulation of VIR-O cells in human disease.

A remaining question is what advantages does the AV-T subpopulation confer to *A. baumannii*? A subset of genes upregulated in the AV-T cells are predicted to be involved in the catabolism of aromatic compounds (ABUW_0066, ABUW_0068, ABUW_0070), generation of free phosphate and sulfur from organic sources (ABUW_0904, ABUW_2921), iron storage (ABUW_3125) and nutrient transport (ABUW_0143, ABUW_3403, ABUW_1660). This raises the possibility that the AV-T subpopulation is better suited for natural environments outside the host, where nutrients are limited and bacteria may rely on the uptake and catabolism of atypical compounds for use as nutrients. Indeed, AV-T cells grew to higher yields in a nutrient poor media (Chamberlain's) relative to VIR-O cells (FIG. 4A). Biofilm formation may facilitate colonization of natural environments, such as in soil and water, and AV-T cells were shown to be more proficient than VIR-O cells at biofilm formation at low temperature (25° C.) (FIG. 4B). Furthermore, at low temperature outside the host, ABUW_1645 expression in AV-T cells was increased, and was subsequently reduced in cells grown at 37° C. (FIG. 4C). Correspondingly, when AV-T cells were grown at host temperature (37° C.) as would occur during infection, their rate of switching to VIR-O cells increased more than 3,400-fold (FIG. 4D). These data are in agreement with those from mouse infections (FIG. 1) and human samples (FIG. 3), in which VIR-O cells vastly outnumber AV-T cells. Taken together, these results suggest that AV-T cells are better suited to survive in certain environmental conditions, and their reduced levels of capsule may even render these cells resistant to bacteriophages (Regeimbal, J. M. et al. Antimicrobial agents and chemotherapy 60 (2016)). This study reveals a phenotypic switch linking resistance to host antimicrobials, virulence and environmental persistence. The data highlight an unexpected role for specific host innate immune antimicrobials (CRAMP, lysozyme and $H_2O_2$) in enriching the virulent VIR-O subpopulation during murine infection. These data clearly demonstrate that the VIR-O cells are responsible for causing disease in vivo. In addition to being the predominant cells recovered from infected mice, VIR-O cells were found in the bloodstream of infected human patients, highlighting their important role in virulence. It is therefore likely that bacterial cells that shed into the environment by infected patients are in the VIR-O form. Interestingly, VIR-O cells also have an increased ability to resist disinfectants and desiccation, two stresses encountered in the hospital environment. This suggests that alarmingly, human infection selects for cells that are best-suited for environmental persistence, and that likewise, the bacterial cells persisting in the environment are those that are most virulent when transmitted to future human hosts. Therefore, the VIR-O subpopulation likely underlies a worrisome cycle present in hospital wards, accounting for the difficulty in eradicating *A. baumannii* as well as the high virulence of many of these infections.

Phenotypic switches that control virulence have been identified in both bacterial and fungal pathogens and this may also represent a bet-hedging strategy where the avirulent subpopulation has a selective advantage outside the host (Slutsky, B. et al. Journal of bacteriology 169, 189-197 (1987); Turner, K. H., Vallet-Gely, I. & Dove, S. L. PLoS genetics 5 (2009); Diard, M. et al. Nature 494, 353-356 (2013); Ronin, I., Katsowich, N., Rosenshine, I. & Balaban, N. Q. eLife 6 (2017); Mouammine, A. et al. Scientific reports 7, 43670 (2017); and Bommanavar, S. B., Gugwad, S. & Malik, N. Journal of oral and maxillofacial pathology 21, 82-86 (2017)). Interestingly, a phenotypic switch in *Photorhabdus luminescens* has similarities to *A. baumannii*, where a virulent subpopulation is more resistant to host antimicrobials (Mouammine, A. et al. Scientific reports 7, 43670 (2017)). In addition, in the eukaryote *Candida albicans*, a phenotypic switch that controls the white-opaque colony transition also has parallels with the *A. baumannii* system, including subpopulation differences in virulence, cell shape and biofilm formation (Bommanavar, S. B., Gugwad, S. & Malik, N. Journal of oral and maxillofacial pathology 21, 82-86 (2017)).

The EnvZ/OmpR two-component system also plays a role in modulating the VIR-O/AV-T switch, as mutations in this pathway result in a hyperswitching phenotype from VIR-O to AV-T (Hiemstra, P. S., McCray, P. B., Jr. & Bals, R. The European respiratory journal 45, 1150-1162, (2015)). However, this is independent of 1645 since: (i) an ompR::Tc mutant and an ompR::Tc 1645 double mutant exhibit similar hyperswitching frequencies, and (ii) 1645 expression is unchanged in an ompR mutant relative to wild-type (FIG. 15). In addition, RNA-Seq data indicated that expression of ompR and envZ were not altered by 1645 overexpression.

Taken together, this data directly shows that the TetR protein 1645 is a master regulator of the VIR-O/AV-T phenotypic switch with an important role in controlling virulence and environmental persistence.

Overexpression of 1645 completely converted VIR-O cells to AV-T cells, and reversed the virulence and environmental persistence attributes of VIR-O cells (FIG. 3). Thus, while the VIR-O/AV-T phenotypic switch is important for facilitating *A. baumannii* virulence, the data suggest that it could be subverted and turned into an "Achilles' heel". Small molecules that drive cells into the AV-T form would render cells avirulent and could represent a potential therapeutic for the treatment of infections. Furthermore, it is demonstrated that the highly attenuated 1645 overexpression strain is a promising live-attenuated vaccine candidate against *A. baumannii*, exerting striking protection against lethal challenge. These findings highlight how knowledge of phenotypic traits endowed by subpopulations of cells can be harnessed to facilitate translational interventions.

Materials and Methods:

Bacterial Strains.

*A. baumannii* strain AB5075 was used in this study. All experiments reported in study were done using the same glycerol stock of VIR-O and AV-T cells that were at least 99.9% pure. For each mouse infection, the bacterial inoculum was checked to verify that each culture maintained the VIR-O or AV-T phenotype. *Escherichia coli* strain EC100D (Epicentre) was used for all cloning experiments.

Methods to Distinguish VIR-O and a V-T Variants.

The ability to distinguish between VIR-O and AV-T variants a stereo (dissecting) microscope that illuminates the plates from below with a light source with an adjustable angle (oblique lighting) was used. A correct light angle is used to observe the opacity differences and an improper light angle can make O colonies look like T and vice-versa. Each microscope should be standardized with VIR-O and AV-T variants to set the proper angle. Colonies should be grown on agar plates composed of 5 g tryptone, 2.5 g yeast extract, 2.5 g sodium chloride and 8 g agar per liter (0.5×LB/0.8% agar). The VIR-O and AV-T phenotypes can be observed on regular LB plates, but it can be much harder to distinguish the variants. Importantly, the VIR-O and AV-T opacity phenotypes can be accurately distinguished at high colony density (~100/plate). At low colony density, both variants will look like VIR-O. In addition, VIR-O colonies typically give rise to translucent sectors after 24 hours. AV-T colonies rarely sector to VIR-O, yet AV-T colonies can have up to 50% VIR-O cells at 48 hours.

Electron Microscopy.

Colonies of bacteria were collected from culture plates and placed in 0.1 M sodium cacodylate (pH 7.4) buffered fixative that contained 2% paraformaldehyde, 2.5% glutaraldehyde, 0.075 grams of ruthenium red, and 1.55 grams of L-lysine acetate. After 20 minutes of fixation on ice, samples were centrifuged and washed twice in sodium cacodylate/ruthenium red buffer. Samples were then fixed for a second time for 2 hours with fixative that did not include the L-lysine acetate. Following two additional sodium cacodylate/ruthenium red buffer washes, samples were placed in 1% osmium tetroxide in sodium cacodylate/ruthenium red buffer for 1 hour at room temperature. The fixed bacterial samples were then washed, dehydrated through a graded ethanol series and placed in 100% ethanol. The samples were infiltrated with a mixture of Eponate 12 resin (Ted Pella, Inc.; Redding, Calif.) and propylene oxide before being placed in pure Eponate 12 resin overnight. Resin-infiltrated bacterial samples were polymerized for 48 hours in a 60° C. oven. The resin-embedded bacterial samples were sectioned to 70-80 nm thick sections using a Leica UltraCut microtome (Leica Biosystems; Buffalo Grove, Ill.) and subsequently stained with 5% uranyl acetate and 2% lead citrate. The ultrathin sections were imaged with a JEOL JEM-1400 transmission electron microscope (JEOL Ltd; Tokyo, Japan) operated at 80 kV and equipped with a Gatan US1000 CCD camera (Gatan; Pleasanton, Calif.).

Mice.

WT C57BL/6J mice were purchased from Jackson Laboratories and used at age 8-10 weeks; age- and sex-matched mice were used. TKO deficient in the gp91 component of the NADPH oxidase, lysozyme and CRAMP, were derived by crossing cybb−/− (gp91, Jackson Laboratories), lysM−/− and cramp−/− (CRAMP; Jackson Laboratories) mice. Mouse sample size was determined based on previous studies that generated highly statistically significant results, while also minimizing the number of animals used (5 mice per group for the majority of experiments). Females were used for the majority of the animal experiments. Male mice were used in some experiments to match available knockout mice. Groups of mice with different genetic backgrounds had to be housed separately, precluding randomization and blinding.

Construction of an ABUW_1645 (TetR) Expression Vector.

To generate an expression plasmid for the ABUW_1645 open reading frame, a 697-bp DNA fragment, which began 60 bp upstream from the predicted ABUW_1645 start codon and ended 82 bp downstream from the predicted ABUW_1645 stop codon, was amplified by PCR using chromosomal DNA from *A. baumannii* strain AB5075 as the template (Phusion Hot Start Polymerase; Thermo Scientific, Waltham, Mass.). Oligonucleotide primers (1645 Exp. 1.1; 5'-GAGTGACGGCATGTCTATCT-3' (SEQ ID NO: 3) and 1645 Exp. 2.2; 5'-CTTATAGCCATAAGTGGTAATTGAG-3' (SEQ ID NO: 4)) were treated with T4 Polynucleotide Kinase (New England Biolabs, Ipswich, Mass.) to add 5'-phosphates prior to PCR amplification. The fragment was purified from an agarose gel slice and ligated (Fast-Link Ligase; Epicentre, Madison, Wis.) into pWH1266 (Tipton, K. A. & Rather, P. N. Journal of bacteriology (2016)) that had been digested with ScaI (New England Biolabs) and subsequently treated with shrimp alkaline phosphatase (New England Biolabs) to dephosphorylate linearized vector. The ligation was transformed into *E. coli* Transformax EC100D competent cells (Epicentre) and plated on LB+Tet$^{10}$ plates, resulting in the expression vector pKT1645.

RNA Isolation and RNAseq Analysis.

Cultures of *A. baumannii* strain AB5075 VIR-O cells harboring empty pWH1266 or pKT1645 and strain AB5075 AV-T cells harboring empty pWH1266 or pKT1645 were grown in LB+Tet$^5$ at 37° C. with shaking to an $OD_{600}$~0.75. The cells were harvested from cultures by centrifugation and RNA was isolated using a MasterPure RNA purification kit according to the manufacturer's protocol (Epicentre). Contaminating DNA was removed by treatment with Turbo DNA-free according to the manufacturer's protocol (Ambion, Waltham, Mass.). RNA concentration was quantified with a NanoDrop ND-1000 spectrophotometer. RNA purity was assessed with qRT-PCR analysis of clpX expression in samples with/out reverse transcriptase.

RNA sequencing and analysis. RNA samples were first depleted of ribosomal RNAs using the RiboZero rRNA Removal kit (Illumina). RNA libraries were prepared using the NEBNext® Ultra™ RNA library prep kit for Illumina (NEB) and run on a single multiplexed HiSeq4000 150PE lane (University of Maryland Genomics Resource Center). Paired-end Illumina libraries were mapped against the *A. baumannii* AB5075-UW genome using Bowtie aligner (v0.12.9) and differential gene expression was quantified by DESeq (v1.5.25 (University of Maryland Genomics Resource Center). Differentially expressed transcripts with ap-value of ≤0.05, FDR≤0.05 and $\log_2$ fold change ≥1.7 were used in this study. Sequence reads were deposited at NCBI under Bioproject no. PRJNA400082 as BioSamples SAMN07562376, SAMN07562377, SAMN07562378, SAMN07562379, SAMN07562380, SAMN07562381, SAMN07562382, SAMN07562383 and SAMN07562384.

Mouse Pulmonary Infection Models.

Approximately $5\times10^7$ CFU (24 hour time point) and $5\times10^8$ CFU (8 hour time point) were administered per mouse for infections to quantify the bacterial load, and approximately $3\times10^8$ CFU were administered for survival experiments. For mouse infections, overnight standing bacterial cultures at room temperature were sub-cultured in LB broth and grown at 37° C. with shaking to an OD600~0.15, washed and re-suspended in PBS. Fifty μL of bacterial inocula were inoculated intranasally (i.n.) to each mouse. Mice were anesthetized with isoflurane immediately prior to intranasal inoculation. At each time point, the mice were sacrificed and the lungs, spleen and liver were harvested, homogenized, plated for CFU on 0.5× LB plates.

Antimicrobial Killing Assays.

An equal mixture of VIR-O and AV-T variants were grown to early-log phase in 2 mL LB broth, or LB with tetracycline 6 μg/mL for strains with plasmids. A 5 μL aliquot of each culture was mixed together in 250 μL of 0.1× tryptone/yeast extract (1 g tryptone, 0.5 g yeast extract/liter). Cells were mixed by vortexing and serial dilutions were plated on 0.5×LB agar plates to assess the initial CFU's for both VIR-O and AV-T variants. Various antimicrobials were then added at the following final concentrations: CRAMP (10 μg/mL), lysozyme (10 mg/mL), LL-37 (15 μg/mL) and $H_2O_2$. (0.01%). Cells were treated for 1 hour and dilutions were plated on 0.5×LB agar plates to enumerate the surviving VIR-O and AV-T variants.

Desiccation Assay.

Overnight standing bacterial at room temperature were sub-cultured in LB broth and grown at 37° C. with shaking to an $OD_{600}$~0.15, washed and re-suspended in PBS. Twenty-five μL bacterial inocula were desiccated on a 96-well flat bottom polystyrene plate at room temperature. At each time point following desiccation, desiccated wells were rehydrated in 100 μL sterile PBS for 30 min, then serially diluted and plated for CFU on 0.5×LB plates to enumerate the surviving VIR-O and AV-T variants.

Sensitivity to Disinfectants.

Overnight standing bacterial cultures at room temperature were sub-cultured in LB broth and grown at 37° C. with shaking to an $OD_{600}$~0.15. Nine hundred ninety microliters of culture were then added to tubes containing 10 μL of the appropriated disinfectants, BZT (Sigma-Aldrich), BAK (Sigma-Aldrich) and CHG (Sigma-Aldrich), respectively. Tubes were incubated at room temperature for 30 min. Cultures were then serially diluted and plated for CFU enumerations.

Construction of an ABUW_1645 Deletion.

Mutant *A. baumannii* strains were generated as described (Hoang, T., Karkhoff-Schweizer, R., Kutchma, A. & Schweizer, H. Gene 212, 77-86 (1998)). The ABUW_1645 deletion was generated by PCR (Phusion polymerase, Thermo-Fisher Scientific) amplification of approximately 2 kbp up- and downstream fragments of the ABUW_1645 gene using *A. baumannii* strain AB5075 genomic DNA as template. Oligonucleotide primers 1645 Up-1.1 (AAAAAGGATCCCTACAGACCTTAAATAACGGTG; SEQ ID NO: 5) and 1645 Down-2.1 (AAAAAGGATCCTGGTCAAACTTTACGTGGT; SEQ ID NO: 6) were designed to contain BamHI restriction sites near the 5' end and were paired with 1645 Up-2 (TGCTCTAAATGAAGCTTCTAA; SEQ ID NO: 7) and 1645 Down-1 (ATAATACTGTCCTAGAT-TAAAAATAAAAGC; SEQ ID NO: 8) primers, respectively. The up- and downstream fragments were gel purified (UltraClean 15 DNA Purification Kit, MoBio Laboratories) and then ligated (Fast-Link DNA Ligation Kit, Epicentre Biotechnologies) to produce an approximately 4 kbp deletion allele. This allele contains a deletion corresponding to amino acids 10 to 180 (92% of the protein sequence) of ABUW_1645. The Δ1645 deletion allele was gel purified after ligation and re-amplified via PCR with 1645 Up-1.1 and Down-2.1 primers. Gel-purified Δ1645 deletion allele and pEX18Tc were digested with BamHI and subsequently gel purified. Digested fragments were ligated and transformed into competent *E. coli* Transformax EC100D cells (Epicentre Biotechnologies). This ligation produced the suicide vector pΔ1645/EX18Tc.

To transfer the deletion allele to the chromosome of *A. baumannii* strain AB5075, suicide vector was electroporated into competent AB5075 cells which had been grown in LB medium and washed with 300 mM sucrose, as described by Choi and Schweizer (Choi, K. & Schweizer, H. Nature Protocols 1, 153-161 (2006)). Integrants were selected on LB+tetracycline (5 μg/ml). Counterselection was carried out at room temperature on LB medium without sodium chloride supplemented with 10% sucrose. Potential mutants were screened by PCR amplification and confirmed by DNA sequencing.

An ompR::Tc/D1645 double mutant was generated by transformation of the D1645 mutant with chromosomal DNA from an ompR::Tc mutant obtained from the University of Washington strain collection.

Biofilm Analysis.

VIR-O and AV-T cells were taken directly from freezer stocks and grown in 2 ml 0.5×LB without shaking at room temperature to an optical density A600 of 0.1. Each tube was then used to inoculate 6 wells of a 96 well microtiter plate with 150 μl of culture. Plates were incubated stationary at 25° C. for 24 hours. Cells were removed for the well and the optical density of each well was read at A600 for cell growth. To stain biofilms, 250 μl of 10% crystal violet was added to each well for 30 minutes. The crystal violet was gently decanted and each well was gently washed 3 times with distilled water. 300 μl of 33% acetic acid was added to each well to solubilize the crystal violet and this was then added to 600 μl 33% acetic acid. The absorbance of sample was read at A585.

Growth of *A. baumannii*. The *A. baumannii* VIR-O and AV-T strains were sub-cultured to an $OD_{600}$ of 0.03 in Chamberlain's Defined Media (Teknova), lysogeny broth (LB) (BD Biosciences), or minimal media (M9) supplemented with 0.2% casamino acids. The iron chelator, 2,2'-dipyridyl disulfide (156 μM) was added as indicated. Sub-cultures were placed at 37° C. with aeration in a Biotek Synergy MX plate reader (Applied Biosystems) and $OD_{600}$ was measure every 30 min for 20 hours.

Statistics.

Statistical analyses were performed using Prism 5 (Graphpad Software). The significance of the mouse experiments was determined with the Mann-Whitney test, and the in vitro experiments were analyzed using the two-tailed unpaired student's t-test (for data with a normal distribution). Experiments were repeated at least two to three times. The replicates shown are biological replicates.

What is claimed is:

1. A method of vaccinating against *Acinetobacter baumannii* comprising administering an *Acinetobacter baumannii* comprising an expression vector comprising a nucleic acid encoding the ABUW_1645 protein, PNLEASFRALRVLHTARDLFKQYGFHKVGVDRIIAESKITKATFYNYFHSKERLIE MCLTFQKDGLKEEVF SIIYSYRELMVFDKLKKIFFLHANLEGLYRLPLQAIFEIEKF YPTAYKVVVDYRNWLVTQIHQLLLTIKATATLEDAYMFLFVIDGAMVQLLSKD RIDERDKLLDYFLIILS (SEQ ID NO: 1) to a subject in need thereof.

2. A method of treating an *Acinetobacter baumannii* infection by administering an *Acinetobacter baumannii* comprising an expression vector comprising a nucleic acid encoding the ABUW_1645 protein, PNLEASFRALRVLHTARDLFKQYGFHKVGVDRIIAESKITKATFYNYFHSKERLIE MCLTFQKDGLKEEVF SIIYSYRELMVFDKLKKIFFLHANLEGLYRLPLQAI- FEIEKF YPTAYKVVVDYRNWLVTQIHQLLL-TIKATATLEDAYMFLFVIDGAMVQLLSKD RIDER-DKLLDYFLIILS (SEQ ID NO: 1) to a subject in need thereof.

3. The method of claim 2, wherein the administering of the *Acinetobacter baumannii* is in combination with one or more an antibiotics or antimicrobial agents.

4. The method of claim 3, wherein the one or more antibiotics is imipenem, meropenem, or colistin.

5. A method of treating colonization or infection, or treating or preventing disease by a *Acinetobacter baumannii* microbe comprising administering a clinically effective dose of an attenuated *Acinetobacter baumannii* to a subject in need thereof, wherein the attenuated *Acinetobacter baumannii* comprises an expression vector expressing the ABUW_1645 protein, PNLEASFRALRVLH-TARDLFKQYGFHKVGVDRII AESKITKATFYNYFHS-KERLIEMCLTFQKDGLKEEVFSIIYSYRELMVFDKLK-KIF FLHANLEGLYRLPLQAIFEIEKEYPT-AYKVVVDYRNWLVTQIHQLLLTIKATATL EDAYMFLFVIDGAMVQLLSKDRIDERDKLLDYF-LIILS (SEQ ID NO: 1).

6. The method of claim 5, wherein the attenuated *Acinetobacter baumannii* is administered orally.

7. The method of claim 5, wherein the attenuated *Acinetobacter baumannii* is administered as a live attenuated *Acinetobacter baumannii*.

* * * * *